US012578264B2

(12) United States Patent
Soderman et al.

(10) Patent No.: US 12,578,264 B2
(45) Date of Patent: Mar. 17, 2026

(54) METHOD AND SYSTEM FOR CLASSIFYING MONITORED MOLECULAR INTERACTIONS

(71) Applicant: CYTIVA SWEDEN AB, Uppsala (SE)

(72) Inventors: Tobias Soderman, Uppsala (SE); Olof Karlsson, Uppsala (SE); Paul E. Belcher, Marlborough, MA (US)

(73) Assignee: CYTIVA SWEDEN AB, Uppsala (SE)

( * ) Notice: Subject to any disclaimer, the term of this patent is extended or adjusted under 35 U.S.C. 154(b) by 698 days.

(21) Appl. No.: 17/998,236

(22) PCT Filed: Jun. 22, 2021

(86) PCT No.: PCT/EP2021/067031
§ 371 (c)(1),
(2) Date: Nov. 8, 2022

(87) PCT Pub. No.: WO2022/002699
PCT Pub. Date: Jan. 6, 2022

(65) Prior Publication Data
US 2023/0228676 A1 Jul. 20, 2023

(30) Foreign Application Priority Data
Jun. 29, 2020 (GB) ..................................... 2009910

(51) Int. Cl.
| | |
|---|---|
| *G01N 21/27* | (2006.01) |
| *G16C 20/50* | (2019.01) |
| *G16C 20/70* | (2019.01) |

(52) U.S. Cl.
CPC ........... *G01N 21/272* (2013.01); *G16C 20/50* (2019.02); *G16C 20/70* (2019.02)

(58) Field of Classification Search
CPC ........ G16C 20/10; G16C 20/50; G16C 20/70; G06N 20/00; G01N 21/272; G01N 21/553
See application file for complete search history.

(56) References Cited

U.S. PATENT DOCUMENTS

| | | | |
|---|---|---|---|
| 2018/0224439 A1 | 8/2018 | Karlsson | |
| 2018/0293511 A1* | 10/2018 | Bouillet | ................. H04L 67/12 |

(Continued)

FOREIGN PATENT DOCUMENTS

| | | |
|---|---|---|
| CN | 111289477 A | 6/2020 |
| EP | 1488237 A1 | 12/2004 |

(Continued)

OTHER PUBLICATIONS

JP Office Action for corresponding JP Application No. 2022-579099, dated Apr. 1, 2025, 2 pages.

(Continued)

*Primary Examiner* — Jennifer Wecker
(74) *Attorney, Agent, or Firm* — Eversheds-Sutherland (US) LLP

(57) ABSTRACT

Disclosed is a method for classifying monitoring results from an analytical sensor system (20), by allowing (100) a first set of analyte sample solutions to interact with a ligand (3) and acquiring (101) a set of response data, extracting (102) at least one interaction parameter from the response data, and for each analyte sample solution providing (103) a trained machine learning algorithm with the interaction parameter(s). The trained machine learning algorithm classifies (104) each analyte sample solution based on the interaction parameter(s) into at least one quality classification group indicative of the interaction of the analyte sample solution with the ligand (3). The machine learning algorithm is trained (200) using a set of interaction parameters extracted from response data obtained from interactions (Continued)

between a second set of analyte sample solutions with at least one ligand (3), and at least one quality classification group indicative of the interaction of the analyte sample solution with the ligand (3).

15 Claims, 11 Drawing Sheets

(56)                    References Cited

U.S. PATENT DOCUMENTS

| | | | |
|---|---|---|---|
| 2018/0341624 A1* | 11/2018 | Soderman ............... | G06F 17/18 |
| 2020/0190568 A1* | 6/2020 | Boroni Martins ..... | G06N 20/10 |

FOREIGN PATENT DOCUMENTS

| | | |
|---|---|---|
| JP | 2005-521054 A | 7/2005 |
| JP | 2015-508175 A | 3/2015 |
| WO | 03/081245 A1 | 10/2003 |
| WO | 2021063950 A1 | 4/2021 |

OTHER PUBLICATIONS

Saetchnikov Vladimir A., Classification of antibiotics by neural network analysis of optical resonance data of whispering gallery modes in dielectric microspheres, Proceedings of SPIE, 2012, vol. 8424, 84240Q. 1-84240Q.
PCT International Search Report and Written Opinion for PCT/EP2021/067031, mailed Sep. 14, 2021 (17 pages).
GB Search Report for GB2009910.7, mailed Dec. 30, 2020 (2 pages).
Seefried Florian et al., "CiRCus: A Framework to Enable Classification of Complex High-Throughput Experiments", Journal of Proteome Research, vol. 18, No. 4, Feb. 25, 2019 (Feb. 25, 2019), pp. 1486-1493.
Fabian Buchwald et al., "Predicting a small molecule-kinase interaction map: A machine learning approach", Journal of Cheminformatics, Biomed Central Ltd, London, UK, vol. 3, No. 1, Jun. 27, 2011 (Jun. 27, 2011), pp. 1-22.
Eric et al., "Computational classification models for predicting the interaction of drugs with P-glycoprotein and breast cancer resistance protein", SAR and QSAR in environmental research, vol. 25 (12), 2014, pp. 939 to 966.

* cited by examiner

Tabs with compounds
filtered by state and the
number of compounds
in each tab

METHOD AND SYSTEM FOR CLASSIFYING MONITORED MOLECULAR INTERACTIONS

CROSS REFERENCE TO RELATED APPLICATIONS

This application claims the priority benefit of PCT/EP2021/067031, filed Jun. 22, 2021, which claims the priority benefit to GB Application No. 2009910.7, filed Jun. 29, 2020, the entire contents of which are incorporated herein by reference.

TECHNICAL FIELD

The present invention relates generally to a method and system for classifying monitored molecular interactions.

BACKGROUND ART

Analytical sensor systems arranged to monitor interactions between molecules, such as biomolecules, in real time are often based on label-free biosensors such as optical biosensors. A representative such biosensor system is the BIACORE® instrumentation, which uses surface plasmon resonance (SPR) for detecting interactions between molecules in a sample and molecular structures immobilized on a sensing surface. A sample is passed over the sensor surface and the progress of binding directly reflects the rate at which the interaction occurs. Injection of a sample is followed by a buffer flow during which the detector response reflects the rate of dissociation of the complex on the surface.

A typical output from the BIACORE® system and similar biosensor systems is a response graph or detection curve describing the progress of the molecular interaction with time, including an association phase part and a dissociation phase part. This response graph or detection curve, which is usually displayed on a computer screen, is often referred to as a binding curve or "sensorgram".

It is possible, with the BIACORE® system (and analogous sensor systems), to determine a plurality of interaction parameters for the molecules used as ligand and analyte. These parameters include kinetic rate constants for binding (association) and dissociation of the molecular interaction as well as the interaction affinity.

At early stages in, for example, fragment-based drug discovery, candidate analytes can seldom be identified reliably from single binding measurements alone. Binding Level Screen (BLS) provides an overview of a library of analyte candidates such that analytes which are relevant for further analysis can be identified. In a typical BLS, a single concentration of each analyte is run over target(s) and reference. Promising analytes can be selected with respect to the binding strength as well as their binding behaviour through analysis of the response data. In the next step, an affinity screen, promising analytes can be tested using a series of concentrations to confirm that binding is concentration dependent and to determine or at least estimate the affinity of the analyte/ligand interaction It is, however, cumbersome and difficult for the user, even for experienced users, to classify which binding level screen (BLS) analyte samples are hits to use for further processing, especially when there can be several hundred in one evaluation. As different users may classify the BLS samples differently (i.e. as hits or not), the evaluation of a library of candidate analytes may vary and be user dependent. In the affinity screen analysis a user may need to exclude some concentrations from the analysis and has to determine what model to use for KD determination (equilibrium dissociation constant between analyte-ligand). As in the BLS case this can be difficult even for experienced users and the results obtained from an affinity screen can be user dependent. By performing either a BLS or an affinity screen analysis or both, analyte candidates for further processing, for example in drug discovery experiments, may be identified.

SUMMARY OF THE INVENTION

It is an object of the present disclosure to provide a simpler and faster, or at least an alternative method for classifying analyte-ligand interactions, such as to identify analyte candidates for further processing in, for example, drug discovery experiments. The method being suitable for classifying large numbers of such molecular interactions. It is also an object to provide an analytical system for performing such classification of molecular interactions.

The invention is defined by the appended independent claims. Non-limiting embodiments emerge from the dependent claims, the appended drawings and the following description.

According to a first aspect there is provided a method for classifying monitoring results from an analytical sensor system arranged to monitor a molecular interaction between an analyte and a ligand, wherein a set of response data representing progress of the molecular interaction with time is acquired. A first set of analyte sample solutions is allowed to, in turn, interact with a ligand and a corresponding set of response data for each monitored molecular interaction is acquired. At least one interaction parameter is extracted from at least a portion of each set of acquired response data, and for each analyte sample solution, a trained machine learning algorithm is provided with the at least one extracted interaction parameter. The trained machine learning algorithm is allowed to classify each analyte sample solution based on the at least one extracted interaction parameter into at least one quality classification group indicative of the interaction of the analyte sample solution with the ligand.

The machine learning algorithm is trained using a set of interaction parameters extracted from at least a portion of acquired sets of response data obtained from interactions between a second set of analyte sample solutions with at least one ligand, and for each analyte sample solution of the second set of analyte sample solutions, at least one respective quality classification group is indicative of the interaction of the analyte sample solution with the ligand.

The molecular interactions monitored may take place at a sensing surface, e.g. of a mass detection biosensor system such as an optical biosensor, wherein one molecule, the ligand, may be attached/immobilised on the sensor surface and the other molecule, the analyte, passed over the sensor surface such that the progress of analyte-ligand binding may be monitored with time. Analytical sensor systems based on other detection principles are also possible, such as electrochemical systems.

The first set of analyte sample solutions may comprise at least one analyte sample solution. The analytes could, for example, be different candidate analytes in a drug-discovery analysis. Normally when performing a Binding Level Screen (BLS) analysis or Affinity screen analysis, hundreds of analyte sample solutions may be analysed to provide an overview of a library of analyte candidates, such that analyte candidates which interact with a specific ligand and seem relevant for further processing can be identified.

Which interaction parameters and how many interaction parameters to extract from the response data and provide to the trained machine learning algorithm may be decided by a user of the analytical sensor system. Alternatively, it may be predetermined in the method which interaction parameters and how many interaction parameters to extract and provide to the trained machine learning algorithm. Generally, a larger number of interaction parameters will return a more reliable classification. Determining which interaction parameters and extracting these parameters may be performed by (an) ANN(s) or expert system(s) trained on a plurality of training sets of response data. Depending on the aim of the analysis and the ligand analysed the number and type of interaction parameters extracted and provided to the trained machine learning algorithm may differ.

An analyte sample solution is classified by the trained machine learning algorithm based on the at least one extracted interaction parameter into at least one quality classification group indicative of the interaction of the analyte sample solution with the ligand.

The number of different quality classification groups may in one example be two, the first group comprising analytes of good enough interaction with the ligand of interest and the second group comprising analytes of poor interaction with the ligand of interest. The group comprising analytes of good enough interaction with the ligand may then be selected for further analysis.

In another example, the number of quality classification groups may be 100, wherein group 1 comprises analytes of poor interaction with the ligand and group 100 analytes of very good interaction with the ligand. The user may regulate the stringency of the method and put a cut-off at for example >50, thereby including only analytes classified in classification groups 51-100 in a further analysis. Again, it depends on the purpose of an analysis/experiment as to what is a good enough quality of an interaction and where to put a cut-off.

That an analyte sample solution(s) is classified into at least one quality classification group indicative of the interaction of the analyte sample solution(s) with the ligand, could here involve a first classification into a main group, such as relevant or not for further analysis, and a second group informing about why the analyte sample solution was classified into the main group, e.g. due to non-specific binding, too low or high refractive index, biding to the ligand is not 1:1, no binding or very low binding response (below a predetermined cutoff line), high or unexpected slope in association, slow dissociation, poor mixing, R>Rmax and the analyte being a super stoichiometric binder, concentrations above KD (the equilibrium dissociation constant between analyte-ligand), too few concentrations to determine KD, unreliable parameters in steady state analysis.

When training the machine learning algorithm a second set of analyte sample solutions is used. The second set of analyte sample solutions may be different from the first set of analyte sample solutions in both number of analyte sample solutions and type of analytes. The ligand(s) used when training the machine learning algorithm may be the same as used for interaction with the first set of analyte sample solutions. The ligand(s) used may alternatively be ligand(s) not used for interaction with the first set of analyte sample solutions.

The second set of analyte sample solutions may comprise a plurality of different analyte sample solutions. Preferably, the second set of sample solutions comprises at least 10, at least 100 or at least 500 different analyte sample solutions.

The larger number of analyte sample solutions used for the training, the better the classification of analyte sample solutions of the first set of analyte sample solutions.

Which interaction parameters and how many interaction parameters per analyte sample solution to use for training of the machine learning algorithm may be dependent on the aim of the use of the machine learning algorithm. Generally, a larger number of interaction parameters used for the training, the better the classification of analyte sample solutions of the first set of analyte sample solutions. Determining which interaction parameters and extracting these parameters may be performed by an expert user of the analytical system or by (an) ANN(s) or expert system(s) trained on a plurality of training sets of response data.

The number and type of interaction parameters used for training the machine learning algorithm may be the same as provided to the trained machine learning algorithm for the analyte sample solutions of the first set of analyte sample solutions. Alternatively, the number and/or type of interaction parameters used may differ. The machine learning algorithm may be trained on a larger set of interaction parameters than is used for the actual classification of the analyte sample solutions of the first set of analyte sample solutions.

The machine learning algorithm is also provided with, for each analyte sample solution of the second set of analyte sample solutions, at least one respective quality classification group indicative of the interaction of the analyte sample solution with the ligand. Determining the quality classification group of each analyte sample solution of the second set of analyte samples may be performed by an expert user of the analytical system or by (an) ANN(s) or expert system(s) trained on a plurality of training sets of response data.

The number of different quality classification groups may in one example be two, the first group comprising analytes of good enough interaction with the ligand of interest and the second group analytes of poor interaction with the ligand of interest. A classification being good enough indicating that such analytes could be of interest for further analysis.

In another example, the number of quality classification groups may be 100, wherein group 1 comprises analytes of poor interaction with the ligand and group 100 analytes of very good interaction with the ligand.

That an analyte sample solution is classified into at least one quality classification group indicative of the interaction of the analyte sample solution with the ligand, could here involve a first classification into a main group, such as relevant or not for further analysis, and a second group informing about why the analyte sample solution was classified into the main group, e.g. due to non-specific binding, too low or high refractive index, binding to the ligand is not 1:1, no binding or very low binding response (below a predetermined cutoff line), high slope in association, slow dissociation, poor mixing, R>Rmax and the analyte being a super stoichiometric binder, concentrations above KD, too few concentrations to determine KD, unreliable parameters in steady state analysis.

Such a trained machine learning algorithm will then return a classification of an analyte sample solution from the first set of analyte sample solutions into a quality classification group indicative of the interaction of the analyte sample solution with the ligand. In a BLS analysis, when hundreds of analyte sample solutions are to be analysed to provide an overview of a library of analyte candidates, the present method would provide a fast classification of analyte candidates as relevant or not for further analysis and in affinity screen the method would provide additional estimates of concentration dependence and affinity (KD). Further, the evaluation of candidate analytes is made less user dependent and not as experienced users may be assisted in the evaluation of monitored molecular interactions.

The at least one interaction parameter extracted from the set of acquired response data for an analyte sample solution of the first set of analyte sample solutions may comprise 80-100% of the acquired response data.

The at least one interaction parameter extracted from the set of acquired response data for an analyte sample solution of the second set of analyte sample solutions and used for training of the machine learning algorithm may comprise 80-100% of the acquired response data.

The at least one interaction parameter extracted from the set of acquired response data for an analyte sample solution of the first set of analyte sample solutions may comprise any one or more the following interaction parameters extracted at defined time points in the response data, a) early binding response,
b) late binding response,
c) stability early response,
d) stability late response,
e) early binding response divided by molecular weight of the analyte,
f) late binding response divided by molecular weight of the analyte,
g) difference of binding late response and binding early response divided with the binding early response,
h) measured variation in any of interaction parameters a)-g),
i) measured slope of any of the interaction parameters a)-g), and/or the interaction parameter comprises, when said analyte sample solution is constituted by a plurality of analyte sample solutions of different analyte concentrations of the same analyte:

j) equilibrium dissociation constant calculated using a maximum binding capacity from said plurality of analyte sample solutions.

Parameter j), the equilibrium dissociation constant, KD, being obtained from an affinity screen analysis obtained from a series of analyte concentrations (i.e. with the same analyte). The maximum binding capacity, Rmax, used may be a constant or fitted Rmax. Where Rmax is the response when all binding sites on the surface is occupied by analyte. Fitted Rmax is when Rmax is used and determined as a free fitted parameter. Constant Rmax is when Rmax is not fitted but entered as a constant to the equation. This can be used when a fitted Rmax is expected to be uncertain but a constant Rmax has been achieved from a more certain determination. For example the Mw (molecular weight) adjusted Rmax fitted with a more high affinity analyte.

The least one interaction parameter extracted from the second set of acquired response data for an analyte sample solution of the second set of analyte sample solutions and used for training of the machine learning algorithm may comprise any one or more the following interaction parameters extracted at defined time points in the response data, a) early binding response,
b) late binding response,
c) stability early response,
d) stability late response,
e) early binding response divided by molecular weight of the analyte,
f) late binding response divided by molecular weight of the analyte,
g) difference of binding late response and binding early response divided with the binding early response, h) measured variation in any of interaction parameters a)-g),
i) measured slope of any of the interaction parameters a)-g), and/or the interaction parameter comprises, when said analyte sample solution is constituted by a plurality of analyte sample solutions of different analyte concentrations of the same analyte:

j) equilibrium dissociation constant calculated using a maximum binding capacity from said plurality of analyte sample solutions.

The method may further comprise for each of the analyte sample solutions of the first set of analyte sample solutions extracting at least one reference subtracted interaction parameter and providing this to the trained machine learning algorithm.

The machine learning algorithm may further be trained using for each of the analyte sample solutions of the second set of analyte sample solutions at least one reference subtracted interaction parameter The method may further comprise for each of the analyte sample solutions of the first set of analyte sample solutions extracting at least one reference interaction parameter and providing the reference interaction parameter(s) to the trained machine learning algorithm, wherein the at least one reference interaction parameter comprises any one or more of:

k) early binding response of reference,
l) late binding response of reference,
m) stability early response of reference,
n) stability late response of reference, and
o) difference of binding late response of reference, and binding early response of reference, divided with the binding early response of reference, and/or the reference interaction parameter comprises, when said analyte sample solution is constituted by a plurality of analyte sample solutions of different analyte concentrations of the same analyte:

p) equilibrium dissociation constant calculated using a maximum binding capacity from said plurality of analyte sample solutions.

The machine learning algorithm may further be trained using, for each of the analyte sample solutions of the second set of analyte sample solutions, at least one reference interaction parameter, wherein the at least one reference interaction parameter comprises any one or more of:

l) early binding response of reference,
l) late binding response of reference,
m) stability early response of reference,
n) stability late response of reference, and
o) difference of binding late response of reference, and binding early response of reference, divided with the binding early response of reference, and/or the interaction parameter comprises, when said analyte sample solution is constituted by a plurality of analyte sample solutions of different analyte concentrations of the same analyte:

p) equilibrium dissociation constant calculated using a maximum binding capacity from said plurality of analyte sample solutions.

The method may further comprise extracting at least one negative control interaction parameter obtained from interaction of a negative control solution with the ligand and providing the at least one negative control interaction parameter to the trained machine learning algorithm.

7

The machine learning algorithm may further be trained using at least one negative control interaction parameter obtained from interaction of a negative control sample solution with the ligand(s).

The method may further comprise extracting at least one positive control interaction parameter obtained from interaction of a positive control sample solution with the ligand and providing the at least one positive control interaction parameter to the trained machine learning algorithm.

The machine learning algorithm may further be trained using at least one positive control interaction parameter obtained from interaction of a positive control sample solution with the ligand(s).

The machine learning algorithm may be selected from a group comprising decision trees, k nearest neighbour (kNN), random forest, K-means, gradient boosting algorithms, artificial neuronal network (ANN), deep learning algorithm, or any combination thereof.

According to a second aspect there is provided analytical sensor system (for detecting molecular binding interactions between an analyte and a ligand and for classifying monitoring results. The system comprising a sensor device comprising a detector for monitoring a molecular interaction between a ligand and an analyte sample solution with time, a data producer unit arranged to produce response data representing the progress of the monitored molecular interaction with time, an extraction unit arranged to extract at least one interaction parameter from at least a portion of the produced response data, and a data processing unit arranged to receive said at least one interaction parameter and to provide a classification of the analyte sample solution into at least one quality classification group indicative of the interaction of the analyte sample solution with the ligand and based on the at least one interaction parameter using a trained machine learning algorithm.

The analytical sensor system may further comprise a training centre for training of the machine learning algorithm by providing the machine learning algorithm with interaction parameters extracted from response data from a plurality of monitored analyte-ligand interactions together with at least one respective quality classification group indicative of the interaction of the analyte with the ligand.

Figure 9A:
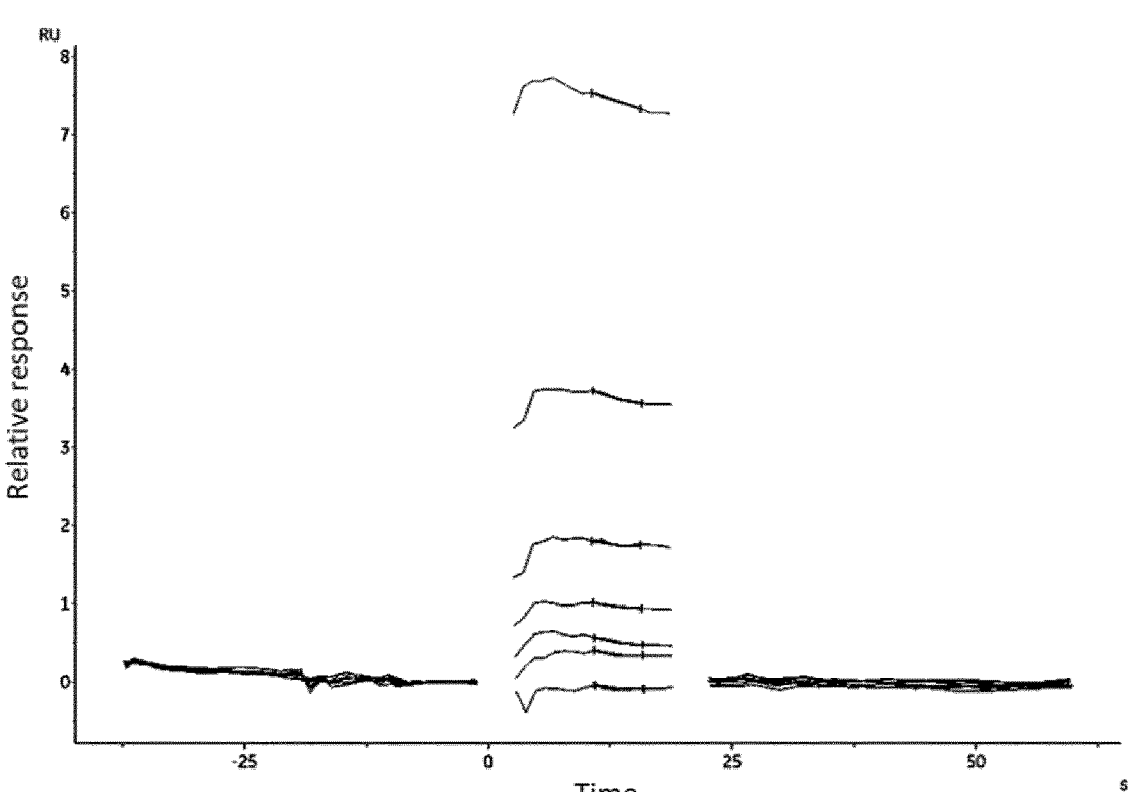
Figure 9B:
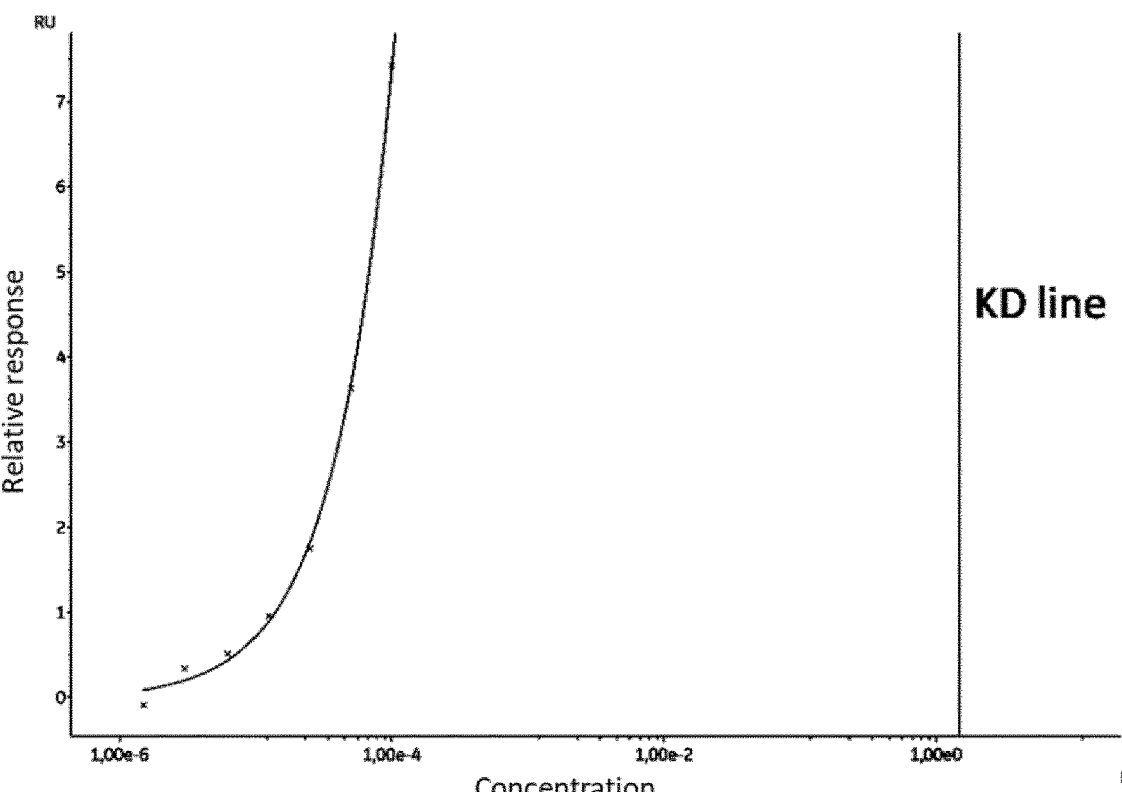
Figure 10:
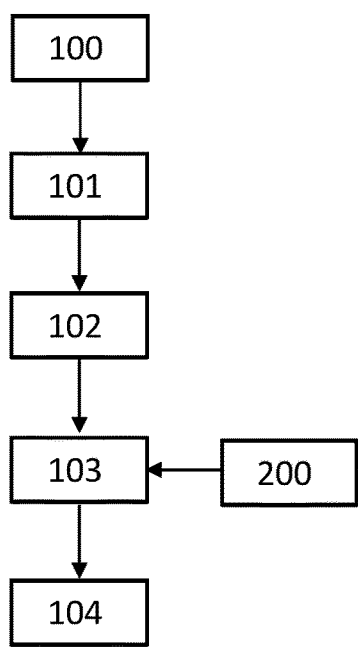

8 below and above KD. This series would be classified into a group for fitting data using free fit of the Rmax parameter FIGS. 9a and 9b show a series of analyte solutions and a dose response curve where all concentrations fall below the KD value when the affinity is determined using a free fit of the Rmax parameter. This series would be classified into a group for fitting data with constant RMax FIG. 10 is a flow chart showing the steps in a method for classifying monitoring results from an analytical sensor system arranged to monitor molecular interactions between an analyte and a ligand.

FIGS. 11 a-e show graphical elements to support training and classification.

DETAILED DESCRIPTION

The present disclosure relates to analytical sensor methods, particularly biosensor based, where molecular interactions are studied. The results are presented in real time, as the interactions progress, in the form of response data, often shown as response curves, sensorgrams.

Biosensors may be based on a variety of detection methods. Typically such methods include, but are not limited to, mass detection methods, such as piezoelectric, optical, thermo-optical and surface acoustic wave (SAW) device methods, and electrochemical methods, such as potentiometric, conductometric, amperometric and capacitance methods. With regard to optical detection methods, representative methods include those that detect mass surface concentration, such as reflection-optical methods, including both internal and external reflection methods, angle, wavelength or phase resolved, for example ellipsometry and evanescent wave spectroscopy (EWS), the latter including surface plasmon resonance (SPR) spectroscopy, Brewster angle refractometry, critical angle refractometry, frustrated total reflection (FTR), evanescent wave ellipsometry, scattered total internal reflection (STIR), optical wave guide sensors, evanescent wave-based imaging such as critical angle resolved imaging, Brewster angle resolved imaging, SPR angle resolved imaging, and the like. Further, photometric methods based on, for example, evanescent fluorescence (TIRF) and phosphorescence may also be employed, as well as waveguide interferometers.

One commonly used detection principle is surface plasmon resonance (SPR) spectroscopy. An exemplary type of SPR-based biosensors is sold under the trade name BIACORE® (hereinafter referred to as "the BIACORE instrument"). These biosensors utilize an SPR based mass-sensing technique to provide a substantially real-time, non-labelled binding interaction analysis between a surface bound ligand and an analyte of interest.

The BIACORE instrument includes a light emitting diode (LED), a sensor chip including a glass plate covered with a thin gold film, an integrated fluid cartridge providing a liquid flow over the sensor chip, and a photo detector array. Incoming light from the LED is totally internally reflected at the glass/gold interface and detected by the photo detector array. At a certain angle of incidence ("the SPR angle"), a surface plasmon wave is set up in the gold layer which is detected as an intensity loss "or dip" in the reflected light. The phenomenon of SPR associated with the BIACORE instrument is dependent on the resonant coupling of monochromatic p-polarized light, incident on a thin metal film via a prism and a glass plate, to oscillations of the conducting electrons, called plasmons, at the metal film on the other side of the glass plate. These oscillations give rise to an evanescent field which extends a distance of the order of one wavelength (~1 μm) from the surface into the liquid flow. When resonance occurs, light energy is lost to the metal film through a collective excitation of electrons therein and the reflected light intensity drops at a sharply defined angle of incidence, the SPR angle, which is dependent on the refractive index within reach of the evanescent field in the proximity of the metal surface.

As noted above, the SPR angle depends on the refractive index of the medium close to the gold layer. In the BIA-CORE instrument, dextran is typically coupled to the gold surface, with the analyte-binding ligand being bound to the surface of the dextran layer. The analyte of interest is injected in solution form onto the sensor surface through the fluid cartridge. Because the refractive index in the proximity of the gold film depends on (i) the refractive index of the solution (which is constant), and (ii) the amount of material bound to the surface, the binding interaction between the bound ligand and analyte can be monitored as a function of the change in SPR angle.

Figure 1:
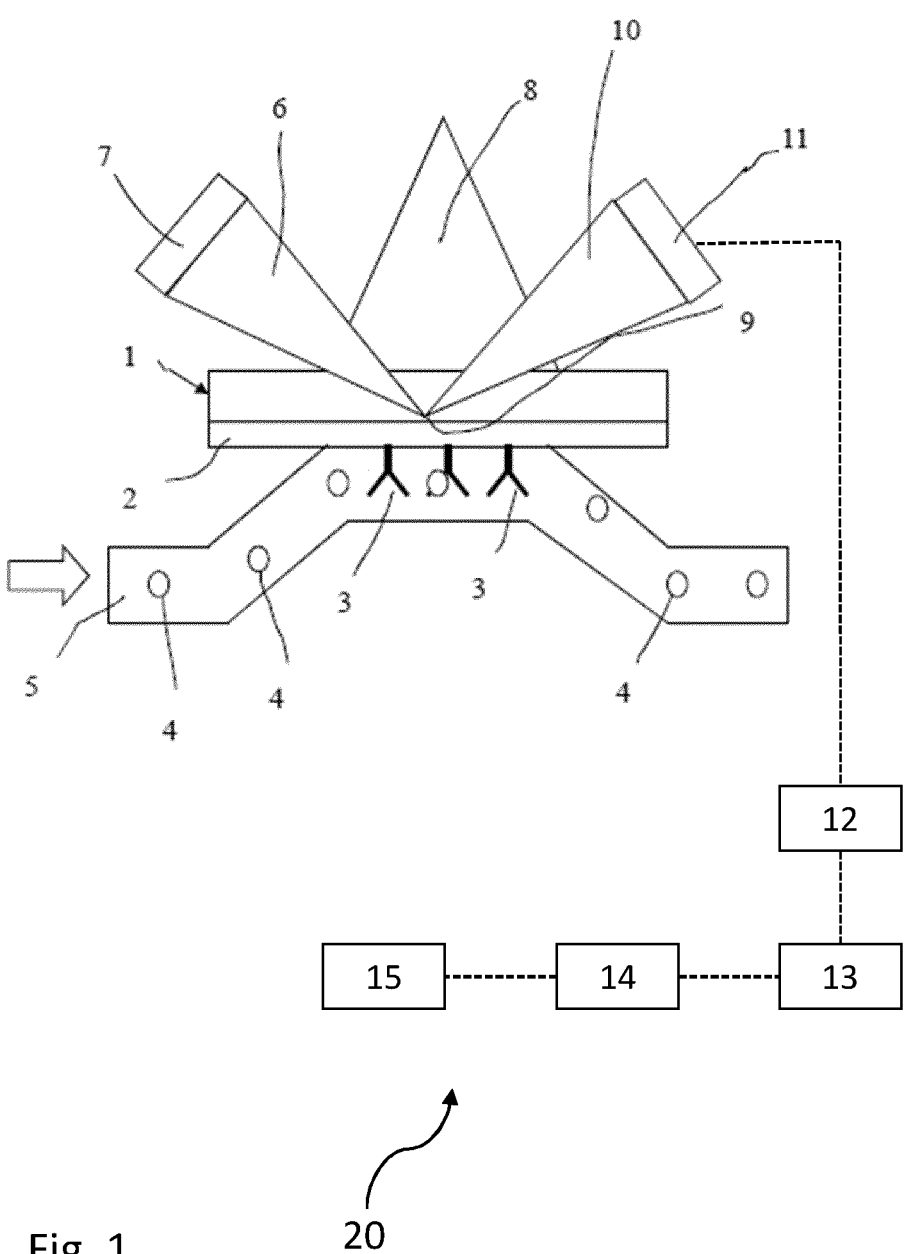
FIG. 1 shows a schematic illustration of an analytical system for detecting molecular binding interactions and classifying monitoring results.

In FIG. 1 is shown a schematic illustration of an analytical sensor system 20 for detecting molecular binding interactions and classifying monitoring results. In this example the system comprises a sensor device, a chip 1, with a sensing surface, a gold film 2, supporting capturing molecules 3, e.g. antibodies, exposed to a sample flow with analytes 4, e.g. an antigen, through a flow channel 5. Monochromatic p-polarised light 6 from a light source 7 (LED) is coupled by a prism 8 to the glass/metal interface 9 where the light is totally reflected. The intensity of the reflected light beam 10 is detected by a detector 11, such as an optical photodetector array.

A typical output from the BIACORE instrument is a "sensorgram", which is a plot of response data (measured in "resonance units" or "RU") as a function of time. An increase of 1,000 RU corresponds to an increase of mass on the sensor surface of about 1 ng per square mm. As sample containing an analyte contacts the sensor surface, the ligand bound to the sensor surface interacts with the analyte in a step referred to as "association." This step is indicated on the sensorgram by an increase in RU as the sample is initially brought into contact with the sensor surface. Conversely, "dissociation" normally occurs when sample flow is replaced by, for example, a buffer flow. This step is indicted on the sensorgram by a drop in RU over time as analyte dissociates from the surface-bound ligand.

Figure 2:
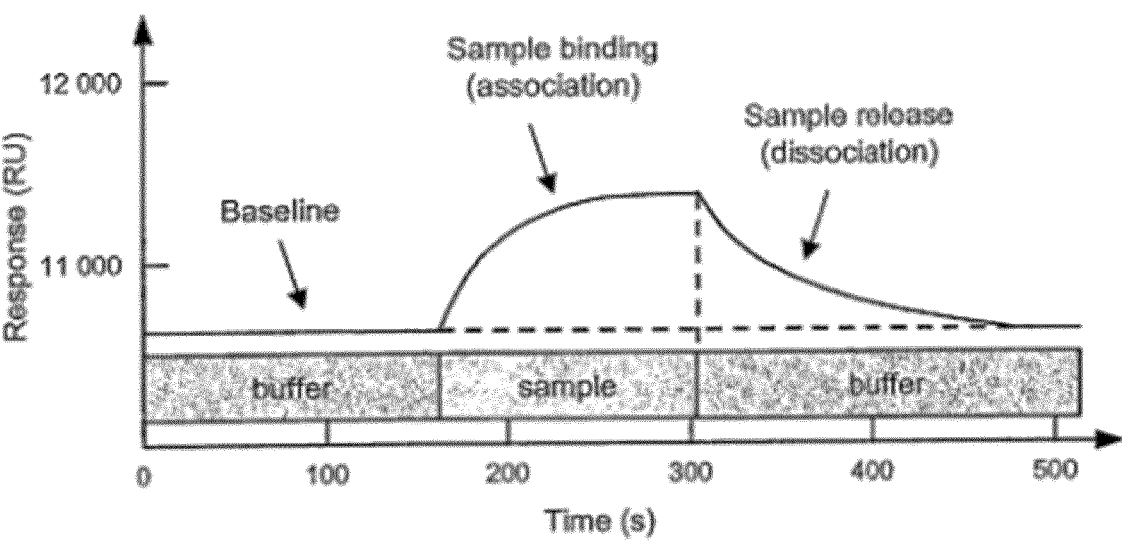
FIG. 2 shows a detection curve from an interaction between an analyte and ligand with time.

A representative sensorgram for the BIACORE instrument is presented in FIG. 2, which depicts a sensing surface having an immobilized ligand (e.g. an antibody) interacting with analyte in a sample. The y-axis indicates the response (here in resonance units (RU)) and the x-axis indicates the time (here in seconds). Initially, buffer is passed over the sensing surface giving the "baseline response" in the sensorgram. During sample injection, an increase in signal is observed due to binding of the analyte (i.e., association) to a steady state condition where the resonance signal plateaus. At the end of sample injection, the sample is replaced with a continuous flow of buffer and a decrease in signal reflects the dissociation, or release, of analyte from the surface. The slope of the association/dissociation curves provides valuable information regarding the interaction kinetics, and the height of the resonance signal represents surface concentration (i.e., the response resulting from an interaction is related to the change in mass concentration on the surface). The analytical system 20 shown in FIG. 1 comprises a data producer unit 12 for producing response data representing the progress of the interactions with time.

The detection curves, or sensorgrams, produced by biosensor systems based on other detection principles will have a similar appearance.

Figure 3:
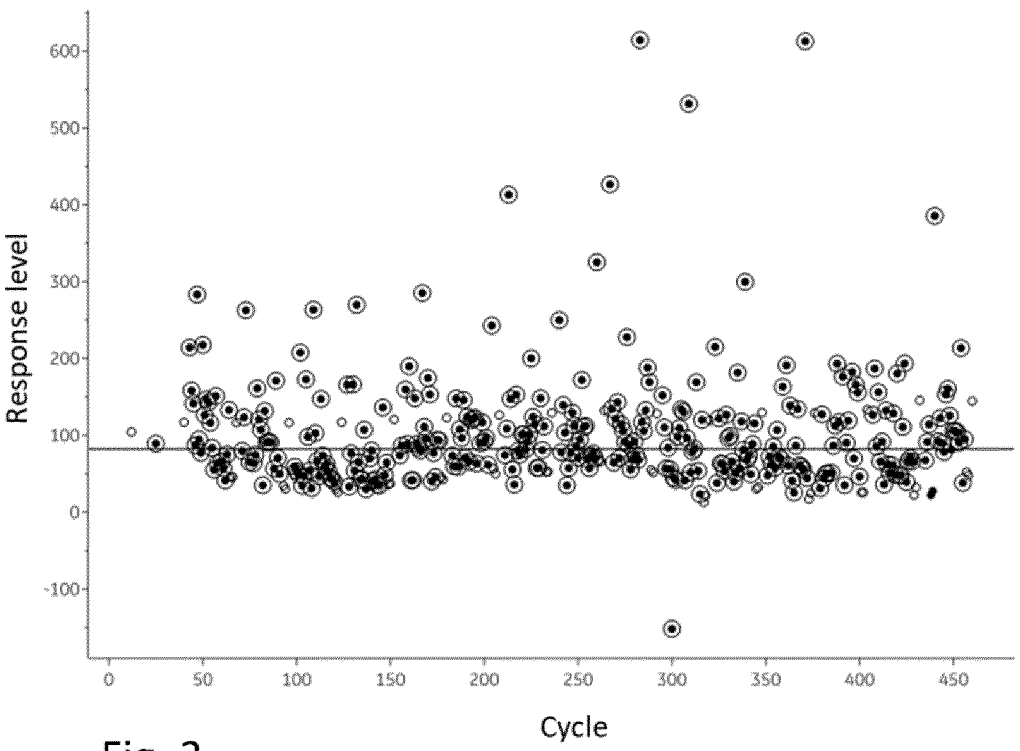
FIG. 3 shows response levels of the binding interaction of a plurality of different analytes of the same concentration with a ligand.

At early stages in, for example, fragment-based drug discovery, candidate analytes can seldom be identified reliably from single binding measurements alone. Binding Level Screen (BLS) provides an overview of a library of analyte candidates such that analytes which are relevant for further analysis can be identified. In a typical BLS, a single concentration of each analyte is run over target(s) and reference. Promising analytes can be selected with respect to the binding strength as well as their binding behaviour through analysis of the response data. In the next step, an affinity screen, promising analytes can be tested using a series of concentrations to confirm that binding is concentration dependent and to determine or at least estimate the affinity of the analyte/ligand interaction It is, however, cumbersome and difficult for the user, even for experienced users, to classify which binding level screen (BLS) analyte samples are hits to use for further processing, especially when there can be several hundred in one evaluation. In FIG. 3 is shown response levels of the binding interaction of a plurality of different analytes of the same concentration with a ligand from a typical BLS analysis. As different users may classify the BLS samples differently (i.e. as hits or not), the evaluation of a library of candidate analytes may vary and be user dependent. In the affinity screen analysis a user may need to exclude some concentrations from the analysis and has to determine what model to use for KD determination.

In affinity screen analysis, acquired sets of response data, sensorgrams, obtained from a series of analyte concentrations (i.e. with the same analyte) are analysed. The machine learning algorithm (ML) may be trained and used for removing outliers among a series of sensorgrams, such that further analysis of the sensorgrams is not based on data including such outlier sensorgrams. If too many sensorgrams in a series is determined to be of poor quality, the whole series should be excluded. The ML determines exclude/include of sensorgrams, and could also be trained by an experts user to include information as to why a specific sensorgram as been excluded.

In affinity screen, classification of sensorgrams may be performed using a plurality of sensorgrams and for each set of sensorgrams a set of features may be calculated and a mathematical model fitted to the set of sensorgrams.

Such calculated set of features may comprise three or more of:

maximum binding capacity, Rmax, divided with a standard error of Rmax, late binding response, B, divided with Rmax, and average mean square error, MSE, between the detection curve and the fitted mathematical model divided with a squared late binding response, $B^2$, and a classification of each sensorgram into a quality classification group.

The maximum binding capacity, Rmax, used may be a constant or fitted Rmax. The equilibrium dissociation constant, KD is fitted.

A set of sensorgrams may comprise at least one sensorgram. When comprising two or more sensorgrams, e.g. 2-10, each sensorgram of a set of sensorgrams represent molecular interactions (between the same ligand and analyte) at different molecular concentrations, i.e. different analyte concentrations.

The mathematical model fitted to a set of sensorgrams is a model which describes molecular interactions at equilibrium. The model may for example be a 1:1 steady state affinity model or a heteropenous ligand steady state affinity model.

The parameter values of KD, Rmax and offset are divided with their respective standard error. The standard error for a parameter is a measure of how significant the parameter is for the closeness of the fitted mathematical model. Rmax may be the calculated Rmax from the fit. The late binding response, B, is the largest binding response in the detection curve relative the baseline in the detection curve. The feature of late binding response, B, may be normalised by dividing it with Rmax and the feature of average mean square error, MSE, is normalised by dividing it with a squared late binding response, $B^2$. The features are normalised to make them applicable for all types of input data. If a steady state model with constant Rmax is applied no standard error can be calculated for this parameter.

The machine learning algorithm may be trained to fit a mathematical model to the set of sensorgrams, calculating a set of features from the set of sensorgrams and the fitted mathematical model and classifying each sensorgram into a quality classification group. The parameters used in the training being determined by an experienced user.

A sensorgram is classified into a quality classification group indicative of the quality of the sensorgram. Poor quality sensorgrams should be excluded from further analysis of the monitored interactions as these may negatively affect the evaluation. Poor quality curves may comprise e.g. a non-stable baseline, air spikes, a response falling below the baseline, etc. and may be caused by for example a contaminated flow system or running buffer, the ligand capturing approach used, or a too low detergent concentration in the running buffer. It depends on the purpose of an analysis/experiment what is a good enough quality of a detection curve and whether to include a detection curve or not in an affinity analysis of the monitored interactions.

The number of different quality classification groups may in one example be two, the first group comprising sensorgrams of good enough quality and the second group sensorgrams of poor quality. The group comprising sensorgrams of good enough quality may then be selected for affinity analysis of monitored molecular interactions.

In another example, the number of quality classification groups may be 100, wherein group 1 comprises sensorgrams of poor quality and group 100 sensorgrams of very good quality. The user may regulate the stringency of the method and put a cut-off at for example >50, thereby including only sensorgrams classified in classification groups 51-100 in a kinetic analysis of a monitored interaction. Again, it depends on the purpose of an analysis/experiment what is a good enough quality of a sensorgram and where to put a cut-off.

The set of features calculated may be three or more. Using a larger number of features in the method may improve the classification of a sensorgram if the features complement each other and highlight something that distinguish what an experienced user regards as distinguishing god enough quality from less good quality. Too many features that do not contribute to the classification may render in less good training and classification. It also possible that additional features, not mentioned above, may be calculated and included in the step of classifying the sensorgrams.

The mathematical model may be selected from a 1:1 steady state affinity or a heterogeneous ligand steady state affinity model.

Based on the classification, which sensorgrams to use in an affinity analysis of the monitored molecular interactions may be determined.

If a fixed/constant Rmax model is used, the fixed level is set to expected Rmax and the evaluation software automatically refits the series after ML prediction. This model predicts fixed Rmax and can be trained by an expert user to annotate why it is fixed Rmax. Fixed Rmax use currently only two features from the sensorgrams and features like slope in association phase and binding early response could be added to detect super stoichiometric cases.

The ML model predicts accept or reject of the series of sensorgrams and why it is a reject. For training of the machine learning algorithm, the expert annotates any predefined subclasses for rejected series, while accepted series are left unmarked. The ML model may consist of two models, one to handle accept/reject and one to handle why it is a reject.

Figure 4A:
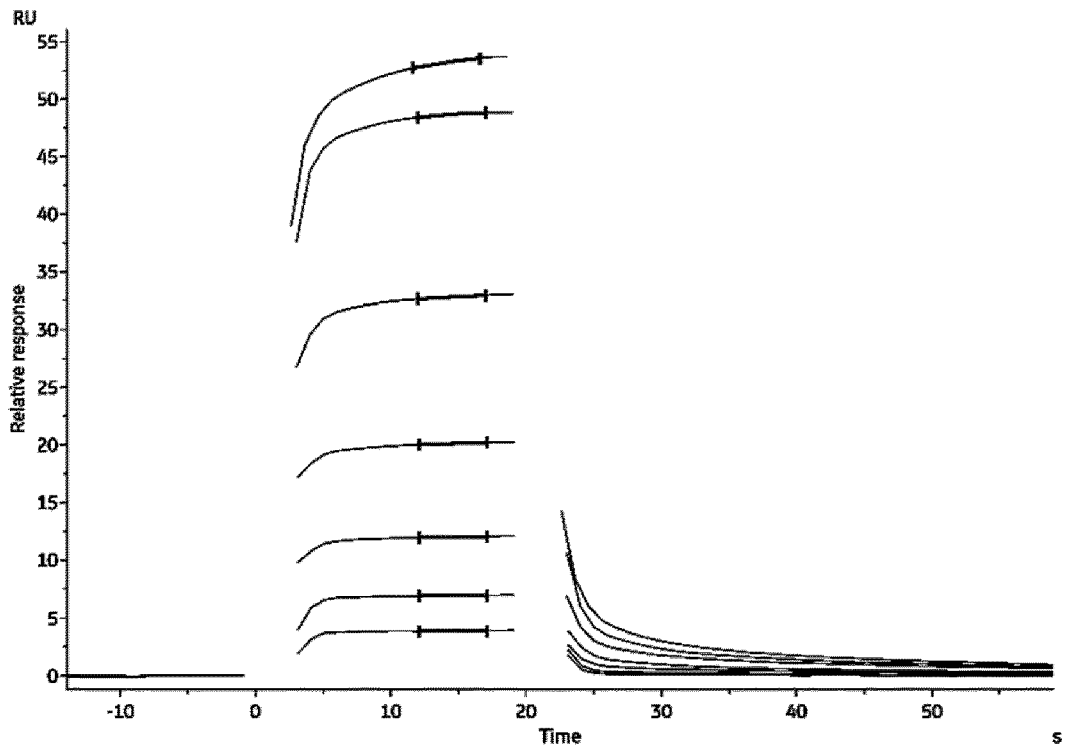
FIGS. 4a and 4b show a concentration series and plot of report point BL concentrations.
Figure 4B:
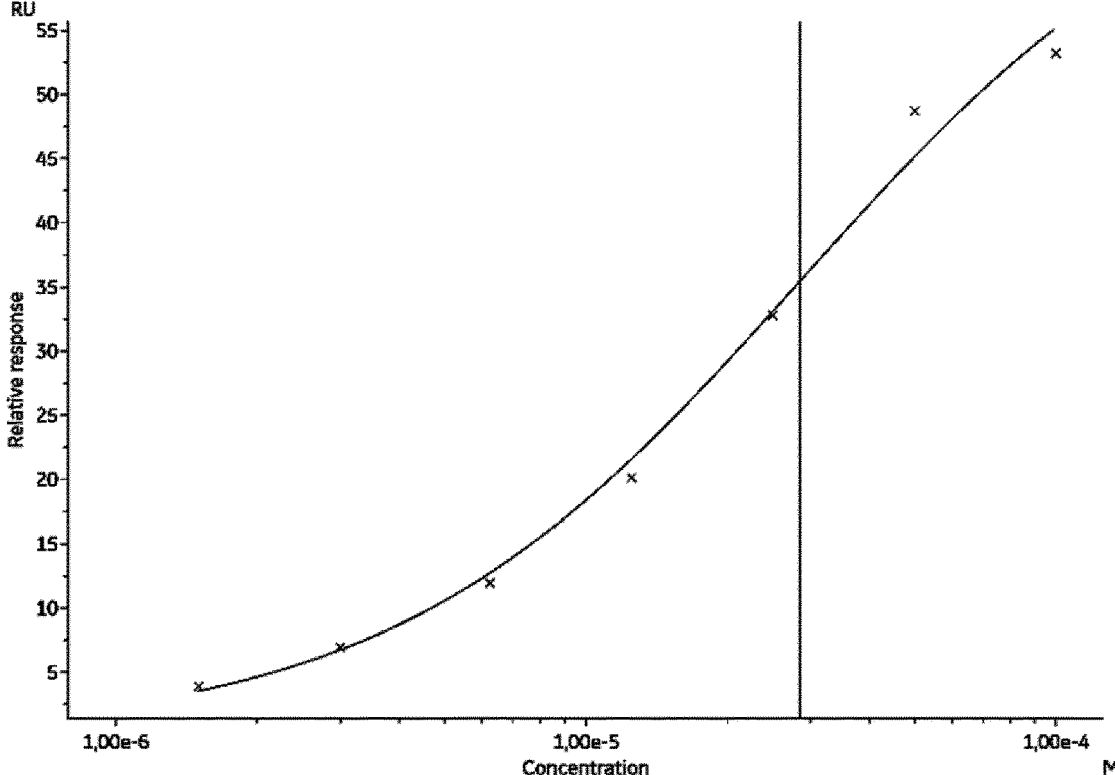

In FIGS. 4a and 4b a concentration series and a report point BL response versus concentration is shown. As in the BLS case this can be difficult even for experienced users and the results obtained from an affinity screen can be user dependent. By performing either a BLS or an affinity screen analysis or both, analyte candidates for further processing, for example in drug discovery experiments, may be identified.

Below is described a method and system for classifying a molecular interaction between an analyte 4 and a ligand 3, such as to identify analyte candidates for further processing in for example drug discovery experiments. The method and apparatus being suitable for classifying large numbers of such molecular interactions.

The method is illustrated in FIG. 10 and an exemplifying analytical sensor system 20 for detecting molecular binding interactions between an analyte 4 and a ligand 3 and for classifying monitoring results in FIG. 1. A first set of analyte sample solutions is allowed 100 to interact with a ligand 3 of interest. The first set of analyte sample solutions may comprise at least one analyte sample solution. The analytes could for example be different candidate analytes in a drug-discovery analysis. Normally when performing a Binding Level Screen (BLS) analysis and Affinity screens hundreds of analyte sample solutions may be analysed to provide an overview of a library of analyte candidates, such that analyte candidates which interact with a specific ligand and seem relevant for further processing can be identified.

A sensor device 1 comprising a detector 11 is arranged to monitor 101 a molecular interaction between a ligand 4 and an analyte 3 sample solution with time. The molecular interactions monitored may take place at a sensing surface 2, e.g. of a mass detection biosensor system such as an optical biosensor, wherein one molecule, the ligand 3, may be attached/immobilised on the sensor surface and the other molecule, the analyte 4, passed over the sensor surface such that the progress of analyte-ligand binding may be monitored with time. Analytical sensor systems based on other detection principles are also possible, such as electrochemical systems.

The analyte sample solutions may comprise approximately the same concentration of analytes. In reality, the exact concentration of an analyte is seldom known. It is possible to allow concentration variations for practical reasons by using a nominal fixed concentration value, but that makes interpretation of results more uncertain.

A data producer unit 12 is arranged to produce corresponding response data representing the progress of the monitored molecular interactions with time. By means of an extraction unit 13 at least one interaction parameter may be extracted 102 from at least a portion of each set of acquired response data. Each set of response data ideally represents molecular interactions between a ligand 3 and an analyte 4. The set of response data may, however, also comprise "noise" due to e.g. unwanted, non-specific, binding to the sensing surface 2, difference in refractive index between the analyte sample solution and the running buffer used.

During analyte sample injection, an increase in signal is observed due to binding of the analyte 4, i.e. association, to a steady state condition where the resonance signal plateaus. Dissociation is when the analyte dissociates from the ligand.

A data processing unit 14 is arranged to be provided 103 with the at least one interaction parameter and to provide 104 a classification of the analyte sample solution into at least one quality classification group indicative of the interaction of the analyte sample solution with the ligand and based on the at least one interaction parameter, using a trained machine learning algorithm.

The response data may be presented as a set of data or graphically as a detection/response curve when using surface plasmon resonance-based biosensors such as BIA-CORE®, a sensorgram.

The at least one interaction parameter may comprise 80-100% of the acquired response data of each detection curve/sensorgram used.

In some embodiments it is preferable to use the whole response data set as the extracted interaction parameter and not just portions thereof. The interaction parameter may for example be based on 90-100% of all response data. The parts of the response data set comprising the most valuable information is response data monitored before the analyte has bound to the ligand, during interaction and for a period after (during dissociation).

The at least one extracted parameter may comprise any one or more of the following interaction parameters extracted at defined time points, such as at defined time intervals, in the response data, a) early binding response,
b) late binding response,
c) stability early response,
d) stability late response,
e) early binding response divided by molecular weight of the analyte,
f) late binding response divided by molecular weight of the analyte,
g) difference of binding late response and binding early response divided with the binding early response,
h) measured variation in any of interaction parameters a)-g),
i) measured slope of any of the interaction parameters a)-g), and/or
the interaction parameter comprises, when said analyte sample solution is constituted by a plurality of analyte sample solutions of different analyte concentrations of the same analyte:
j) equilibrium dissociation constant calculated using a maximum binding capacity from said plurality of analyte sample solutions.

Such a defined time interval may comprise consecutive response data monitored during e.g. 1 second, during 30 seconds, or monitored during 1 minute or more. Preferably during 1 second to 1 minute.

Early binding response for an analyte is the binding level of a detected molecular interaction at the beginning of an analyte sample solution injection. This is when the analyte sample solution is allowed to start to interact with the ligand.

Late binding response for an analyte is the binding level of a detected molecular interaction at the end of an analyte sample solution injection.

The stability early response is the level for each detected molecular interaction at the beginning of the dissociation phase following the analyte sample solution injection.

The stability late response is the level for each detected molecular interaction at the end of the dissociation phase following the analyte sample solution injection.

Figure 5:
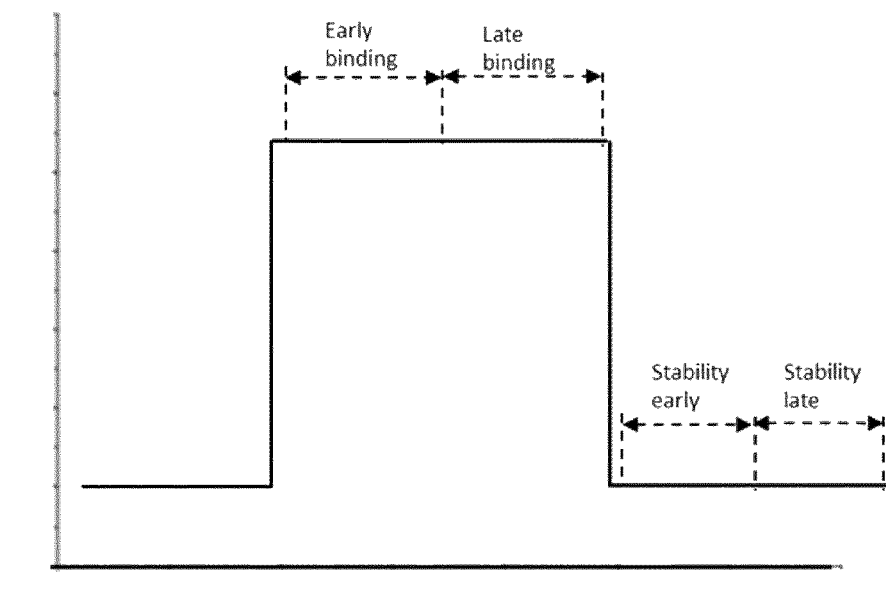
FIG. 5 shows an ideal detection curve wherein the features late binding response, early binding response, stability early and stability late are indicated.

In FIG. 5 is illustrated an ideal detection between an analyte sample solution and a ligand. In this detection curve early binding response, late binding response, stability early and stability late are indicated.

One calculated feature may be the early binding response divided by molecular weight of the analyte. By dividing with the molecular weight the response level is normalized, since a small analyte will not have the same larger response as a larger analyte. The relative response should be as independent on analyte 4 size as possible.

The difference between analyte binding late response and analyte binding early response divided with the analyte binding early response describes the slope in the whole association phase.

A measured variation in any of interaction parameters a)-g), is here meant that a standard variance is taken for the interval between which a certain parameter is measured, for example the parameter early binding response.

A measured slope of any of the interaction parameters a)-g), is here meant that a slope is taken for the interval between which a certain parameter is measured, for example the parameter early binding response.

The number of interaction parameters provided to the trained machine learning algorithm for each analyte sample solution of the first set of analyte sample solutions may be one or more of these parameters. For example, early binding response and difference of binding late response and binding early response divided with the binding early response or late binding response may be used. In an affinity screen the plot of a response from early binding, late binding, stability early or stability late versus concentration provides data that can be fitted with steady state models to obtain KD values.

Which interaction parameters and how many interaction parameters to extract from the response data and provide to the trained machine learning algorithm may be decided by a user of the analytical sensor system. Alternatively, it is predetermined in the method which interaction parameters and how many interaction parameters to extract and provide to the machine learning algorithm. Generally, a larger number of interaction parameters will return a more reliable classification. Determining which interaction parameters and extracting these parameters may be performed by (an) ANN(s) or expert system(s) trained on a plurality of training sets of response data. Depending on the aim of the analysis and the ligand analysed the number and type of interaction parameters extracted and provided to the trained machine learning algorithm may differ. Using a larger number of interaction parameters in the method may improve the classification performed by the trained machine learning algorithm if the interaction parameters complement each other and highlight something that distinguish what an experienced user regards as distinguishing a relevant analyte from a non-relevant analyte. Too many parameters that do not contribute to the classification may render a less good classification. It also possible that additional parameters, not mentioned above, may be calculated and included in the step of classifying the analyte samples solutions.

Alternatively, one or more of these interaction parameters may be provided to the trained machine learning algorithm together with the interaction parameter discussed above comprising 80-100% of the acquired response data for an analyte sample solution of the first set of analyte sample solutions.

An analyte sample solution is classified by the trained machine learning algorithm based on the at least one extracted interaction parameter into at least one quality classification group indicative of the interaction of the analyte sample solution with the ligand.

Analyte sample solutions may be classified with respect to their binding strength as well as to their binding behaviour.

The number of different quality classification groups may in one example be two, the first group comprising analytes of good enough interaction with the ligand of interest and the second group analytes of poor interaction with the ligand of interest. The group comprising analytes of good enough interaction with the ligand may then be selected for further analysis.

In another example, the number of quality classification groups may be 100, wherein group 1 comprises analytes of poor interaction with the ligand and group 100 analytes of very good interaction with the ligand. The user may regulate the stringency of the method and put a cut-off at for example >50, thereby including only analytes classified in classification groups 51-100 in a further analysis. Again, it depends on the purpose of an analysis/experiment what is a good enough quality of an interaction and where to put a cut-off.

Figure 6:
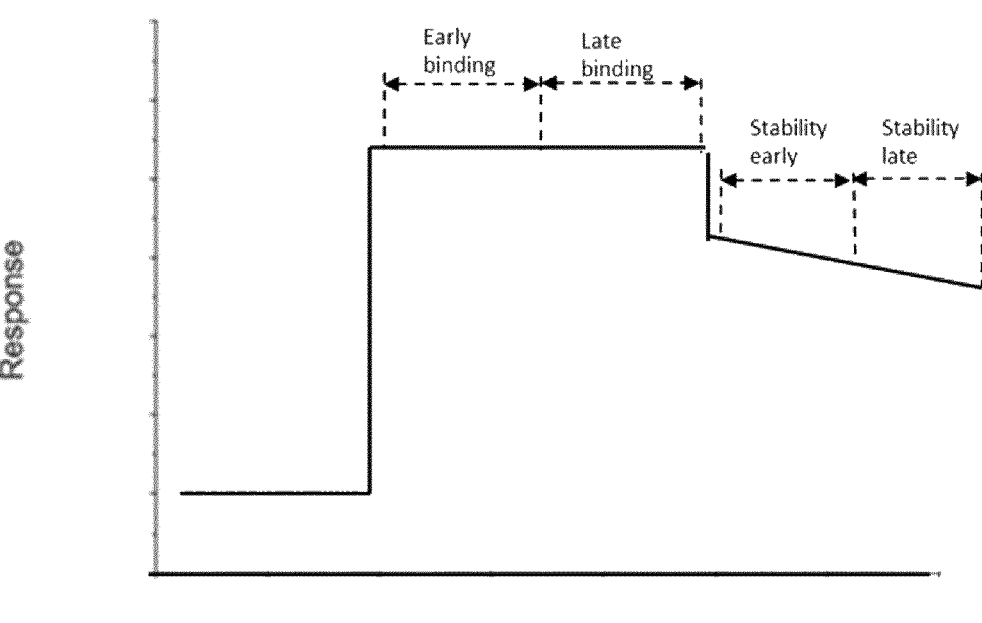
FIG. 6 shows an example of a detection curve showing the binding of an analyte to a ligand wherein the binding is of poor quality.
Figure 7:
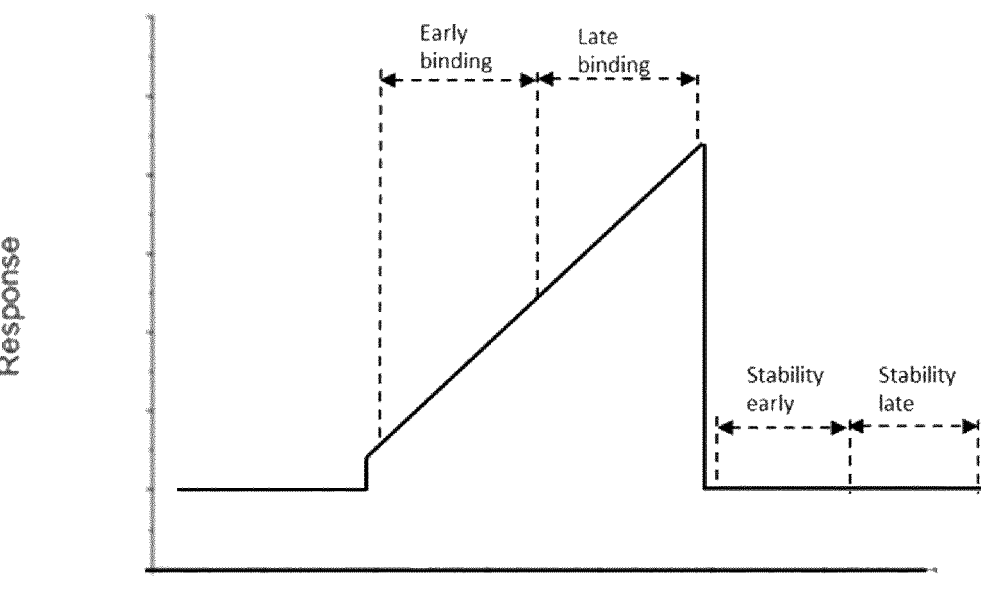
FIG. 7 shows an example of a detection curve showing the binding of an analyte to a ligand wherein the binding is of poor quality.
Figure 8A:
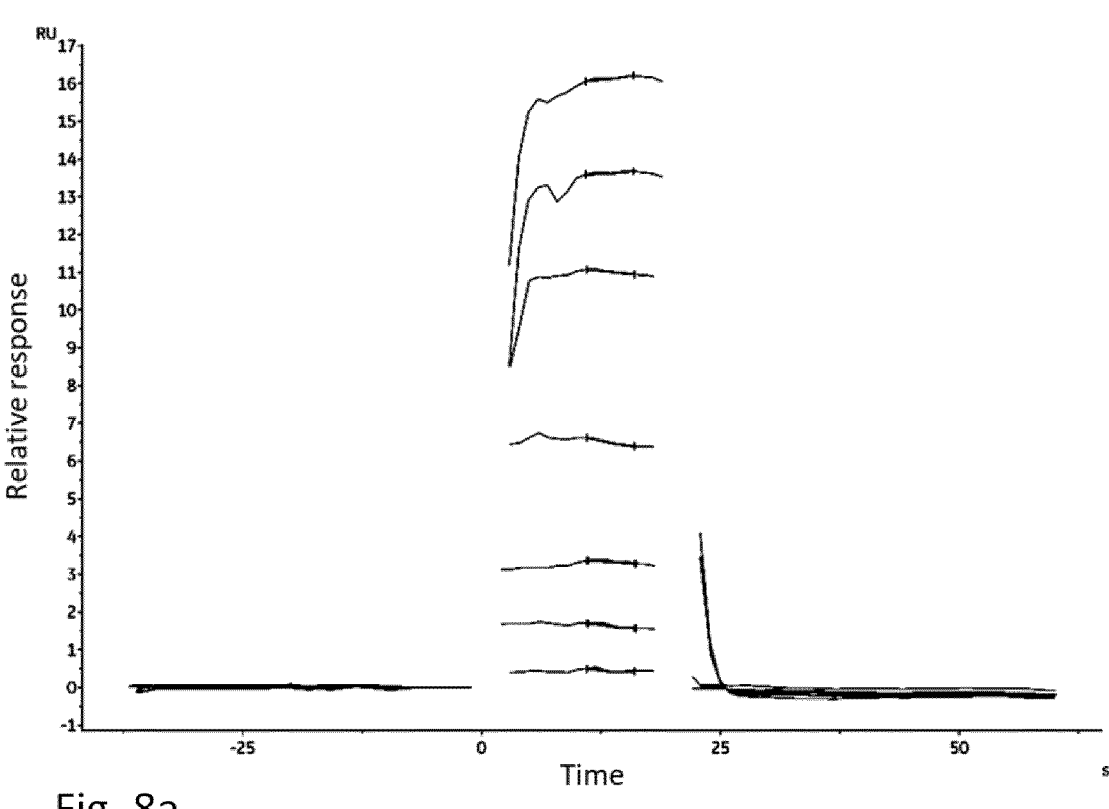
FIGS. 8a and 8b show a series of analyte solutions and a dose response curve where concentrations are present both
Figure 8B:
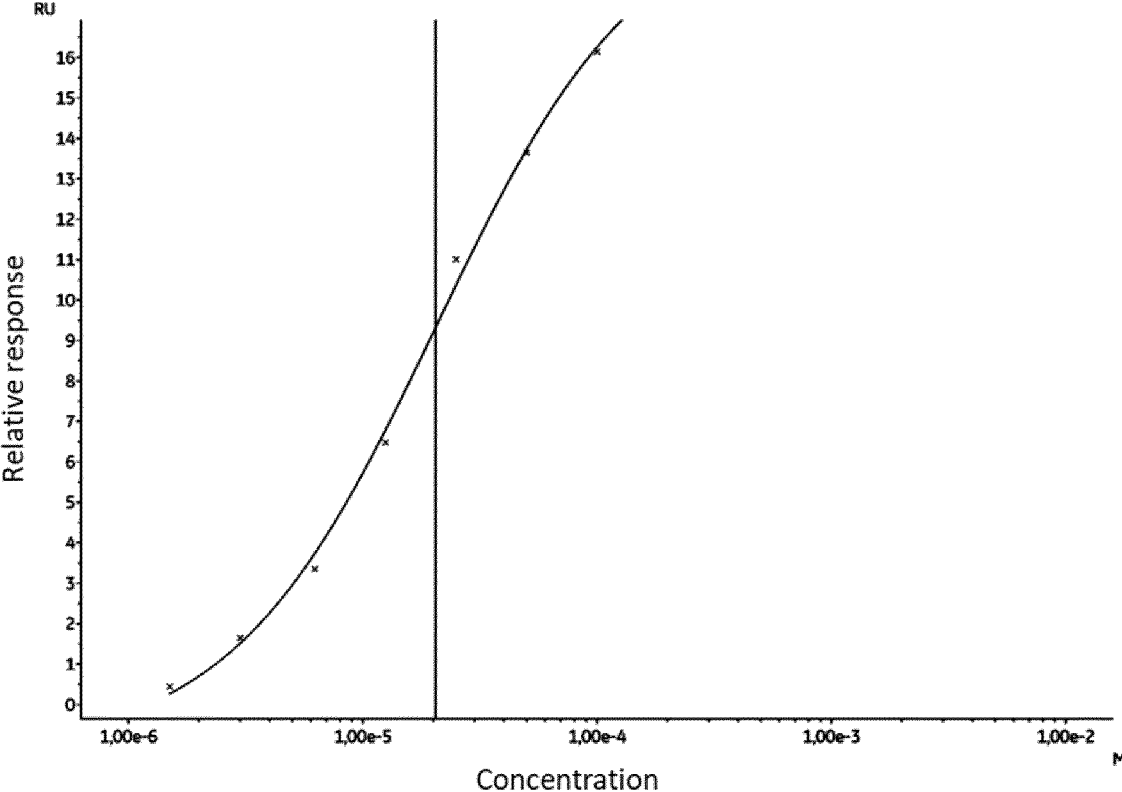

That an analyte sample solution is classified into at least one quality classification group indicative of the interaction of the analyte sample solution with the ligand, could here involve a first classification into a main group, such as relevant or not for further analysis, and a second group informing about why the analyte sample solution was classified into the main group, e.g. due to non-specific binding, too low or high refractive index, binding to the ligand is not 1:1, no binding or very low binding response (below a predetermined cut line), high slope in association, slow dissociation, poor mixing, R>Rmax and the analyte being a super stoichiometric binder. Illustrated in FIG. 5 is an ideal detection between an analyte 4 sample solution and a ligand 3. In this detection curve early binding response, late binding response, stability early and stability late are indicated. In FIGS. 6 and 7 are illustrated curves showing poor quality analyte-ligand bindings. The analyte sample solution of FIG. 6, which shows a lingering response after injection, would for example be classified into a main group as not being relevant for further analysis, and into a second group as showing a secondary unwanted binding of the analyte to the ligand and/or aggregation of the analyte. The analyte sample solution of FIG. 7, which shows an increasing binding of analyte to the ligand during injection, would for example be classified into a main group as not being relevant for further analysis, and into a second group as showing a secondary unwanted binding of the analyte to the ligand and/or aggregation of the analyte. Illustrated in FIGS. 8a and 8b is a series of analyte solutions where a fit of plotted data reveals that concentrations are present both below and above the KD value and where at least one concentration is close to the saturating response. This indicates that KD can be obtained by fitting an Rmax parameter in a steady state model. This series would be classified into a group for fitting data using free fit of the Rmax parameter. In FIGS. 9a and 9b a dose response curve is illustrated where all concentrations fall below the KD value and where the initial fitting procedure returns unreliable KD and Rmax values. This series would be classified into a group for fitting data with constant Rmax parameter.

Other interaction parameters than the ones discussed above may be extracted and used in the method, alone or in combination with these. For example, the method may further comprise for each of the analyte sample solutions of the first set of analyte sample solutions extracting at least one reference subtracted interaction parameter and providing this to the trained machine learning algorithm.

The reference subtracted interaction parameter may be obtained by allowing the first set of analyte sample solutions to interact with a reference without ligand (such as a reference surface without any immobilised ligand) and subtracting the extracted reference interaction parameter from the corresponding extracted interaction parameter Reference interaction parameters may be used in the method, wherein the at least one reference interaction parameter comprises any one or more of:

k) early binding response of reference, l) late binding response of reference, m) stability early response of reference, n) stability late response of reference, and o) difference of binding late response of reference, and binding early response of reference, divided with the binding early response of reference, and/or the interaction parameter comprises, when said analyte sample solution is constituted by a plurality of analyte sample solutions of different analyte concentrations of the same analyte:

p) equilibrium dissociation constant calculated using a maximum binding capacity from said plurality of analyte sample solutions.

A reference interaction parameter may be obtained by allowing the first set of analyte sample solutions to interact with a reference without ligand (such as a reference surface without any immobilised ligand) and extract reference interaction parameter(s) from the thus formed set of reference response data. Such interaction parameters may be added in the method to improve the possibility to detect non-specific binding or poor mixing.

Negative control interaction parameters obtained from interaction of a negative control solution with the ligand may be used in the method.

The at least one negative control solution may comprise an analyte with known non-affinity to the ligand or may comprise no analyte and could for example be a buffer solution. A negative control interaction parameter may for example be a negative control-based boundary level. This is the average response level when injecting negative control multiplied by a defined number of standard deviations, typically three, and defines the binding level limit at which existence of molecular interaction cannot be confirmed. Interaction parameters comprising the negative control aim for detecting poor handling of buffer matching between samples and system running buffer, contamination of samples and/or system, changes of the ligand, experimental signals not related to molecular interactions. The negative controls also determine boundary level, which is used to distinguish interesting hit candidates from non-binders (below boundary).

Positive control interaction parameters obtained from interaction of a positive control sample solution with the ligand may be used in the method.

The at least one positive control solution comprises an analyte sample with known affinity, binding-behaviour, to the ligand. The positive control may have the same molecular concentration as the analyte sample solutions, but in practice this is rare. A positive control interaction parameter may for example be a positive control based boundary level, which is the average binding level for each detected molecular interaction between the ligand and the positive control and defines a known binding level to which unknown samples can be related or establish the stoichiometry of the unknown samples in case where the stoichiometry of the positive control is established. Positive control interaction parameter aims for monitoring the binding capacity of the immobilized target, repeatability of the responses and setting the stoichiometric response level.

In addition to using the above discussed interaction parameters, it may be necessary to, when using surface plasmon resonance based analytical systems such as Bicore®, provide the trained machine learning algorithm during classification of analyte samples with solvent corrected interaction parameters. The need for solvent correction may arise when the amount of ligand is large (compared with a reference without ligand) and the bulk refractive index contribution of the solvent is high compared with the expected analyte response. Bulk solution is excluded from the volume occupied by ligand on the active surface, so that bulk contributions on the active and reference surface will be slightly different, introducing a small error in the reference-subtracted response. As long as the refractive index of the samples is constant, the error in the reference subtracted response is also constant and may be ignored for practical purposes. However, if the refractive index of the samples varies, the magnitude of the error will also vary. Addition of 1% DMSO to buffer gives a bulk response of about 1200 RU, so that small variations in the DMSO content lead to significant variations in the bulk response, in relation to the expected response from low molecular weight samples (which may be down to 1 RU). Such variations are difficult to avoid in the preparation of samples such as fragments and drug candidates for screening applications.

Solvent correction may be determined by injecting a series of blank samples containing a range of solvent concentrations over the active and reference surfaces. A plot of the relative reference-subtracted response on the active surface against the absolute response on the reference surface calibrates the error in reference subtraction against the bulk contribution. This calibration is then used to correct the measured sample responses. It is recommended that solvent correction cycles are run at the beginning and end of a run and at regular intervals during the run. In this way, any given sample cycle will lie between two solvent correction cycles. The correction factor for a given sample cycle is determined by interpolation between the curves from preceding and following correction cycles, to compensate for any drift in the solvent correction factors during the course of the run.

The analytical sensor system 20 may further comprise a training centre 15 for training of the machine learning algorithm. The machine learning algorithm is trained using a set of interaction parameters extracted from at least a portion of acquired sets of response data obtained from interactions between a second set of analyte sample solutions with at least one ligand, and for each analyte sample solution of the second set of analyte sample solutions, at least one respective quality classification group indicative of the interaction of the analyte sample solution with the ligand.

A trained machine learning algorithm mimic the way of classifying an analyte sample solution into a quality classification group of an experienced user. The training may be standard machine learning algorithm training comprising dividing a whole data set into a training and verification set, where 80% of the data is used for training and 20% of the data is used for verification. The machine learning algorithm should be trained on the training data and never on the verification set.

Figure 11A:
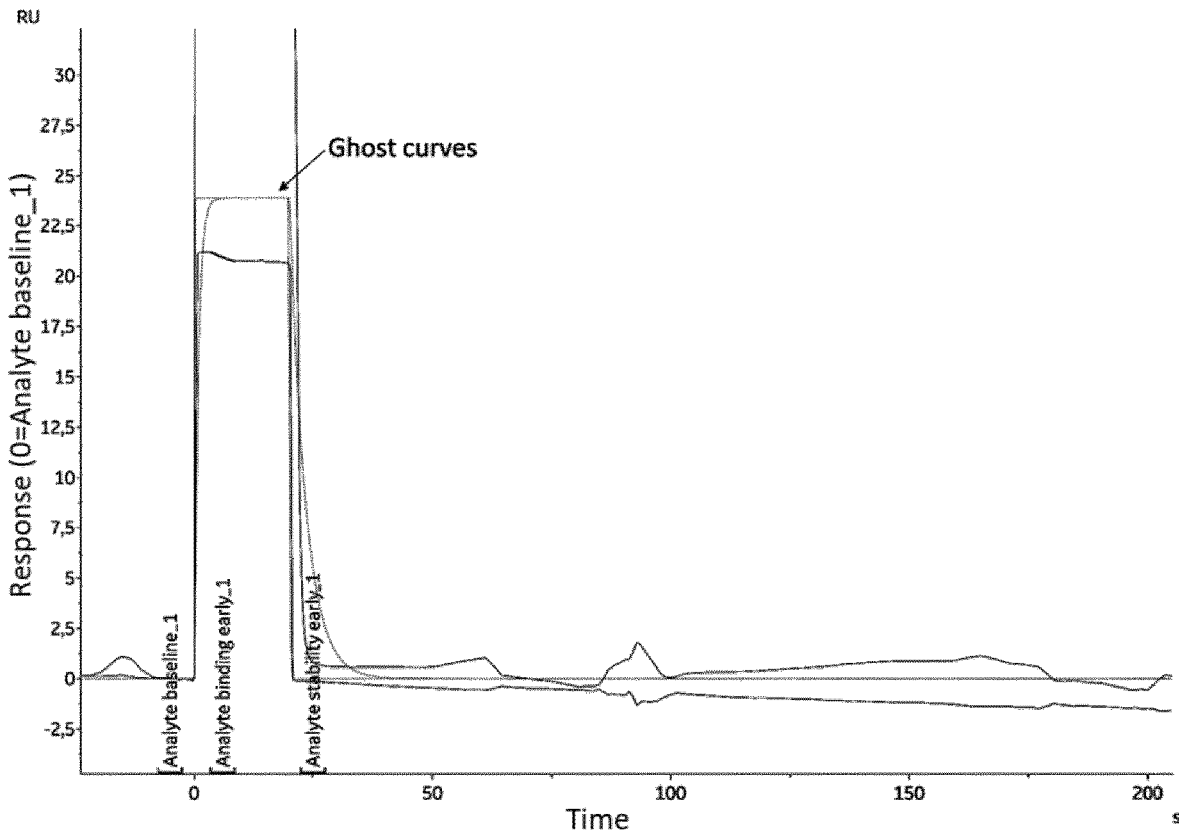
Figure 11B:
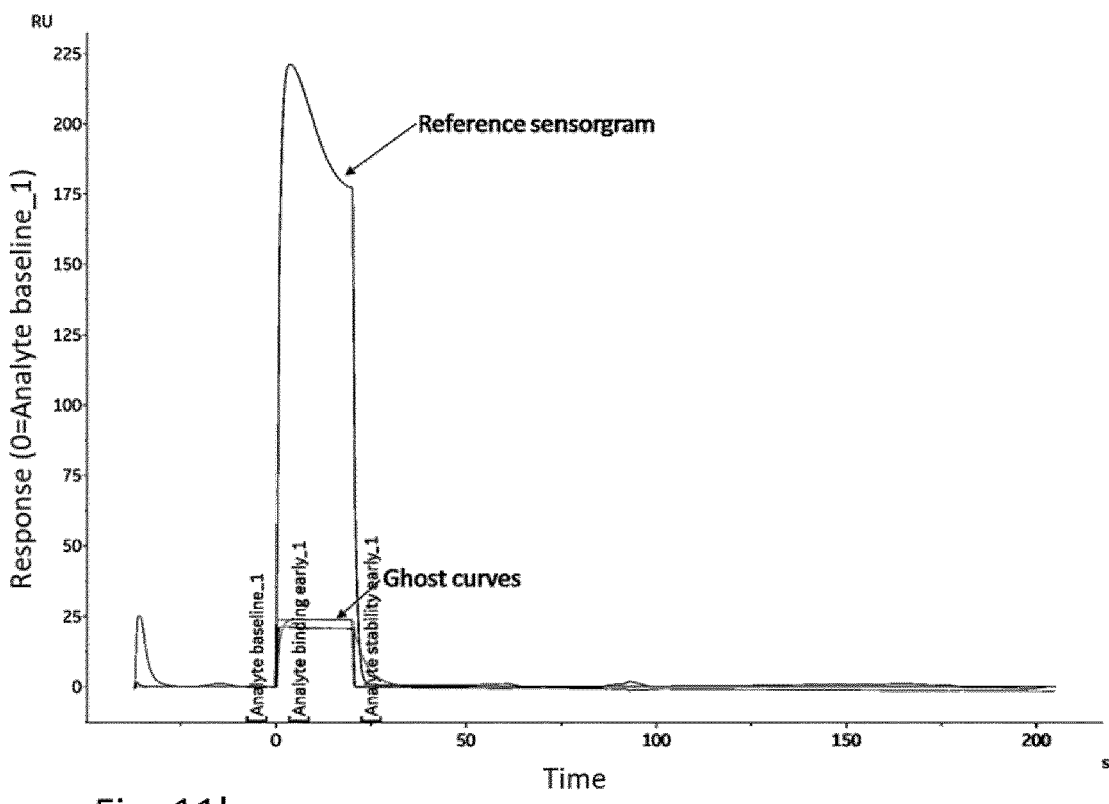
Figure 11C:
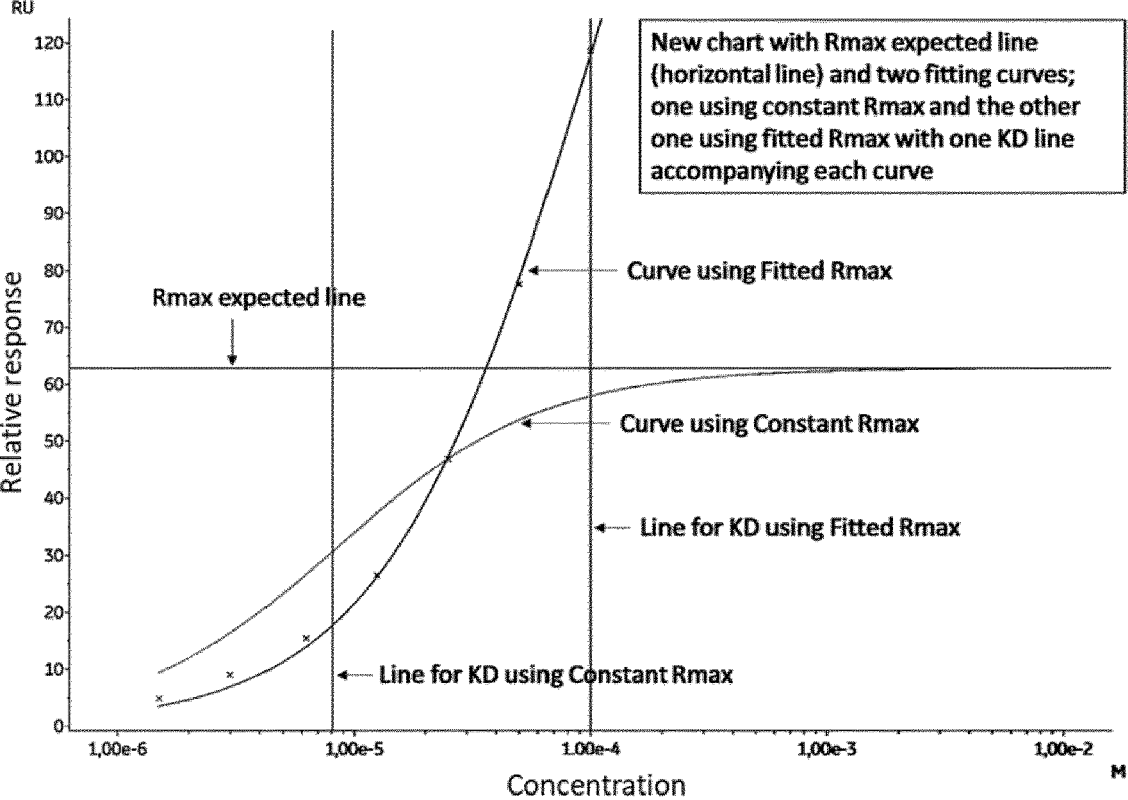

The machine learning algorithm may further be trained using graphical elements as shown in FIGS. 11a-11c to support parameter assignment including comparison to theoretical binding curves, simultaneous display of binding and binding to reference, lines in a dose response plot corresponding to KD values based on the use of different steady state models. By the model generated, classifications can easily by changed through graphical elements as shown in FIG. 11e.

In FIGS. 11a and 11b, ghost curves are indicated in the sensorgrams. Ghost curves are typical fragment profiles simulated with a 1:1 binding model including mass transfer. The Rmax is scaled to enable direct comparison of actual sensorgrams and simulated curves.

Figure 11D:
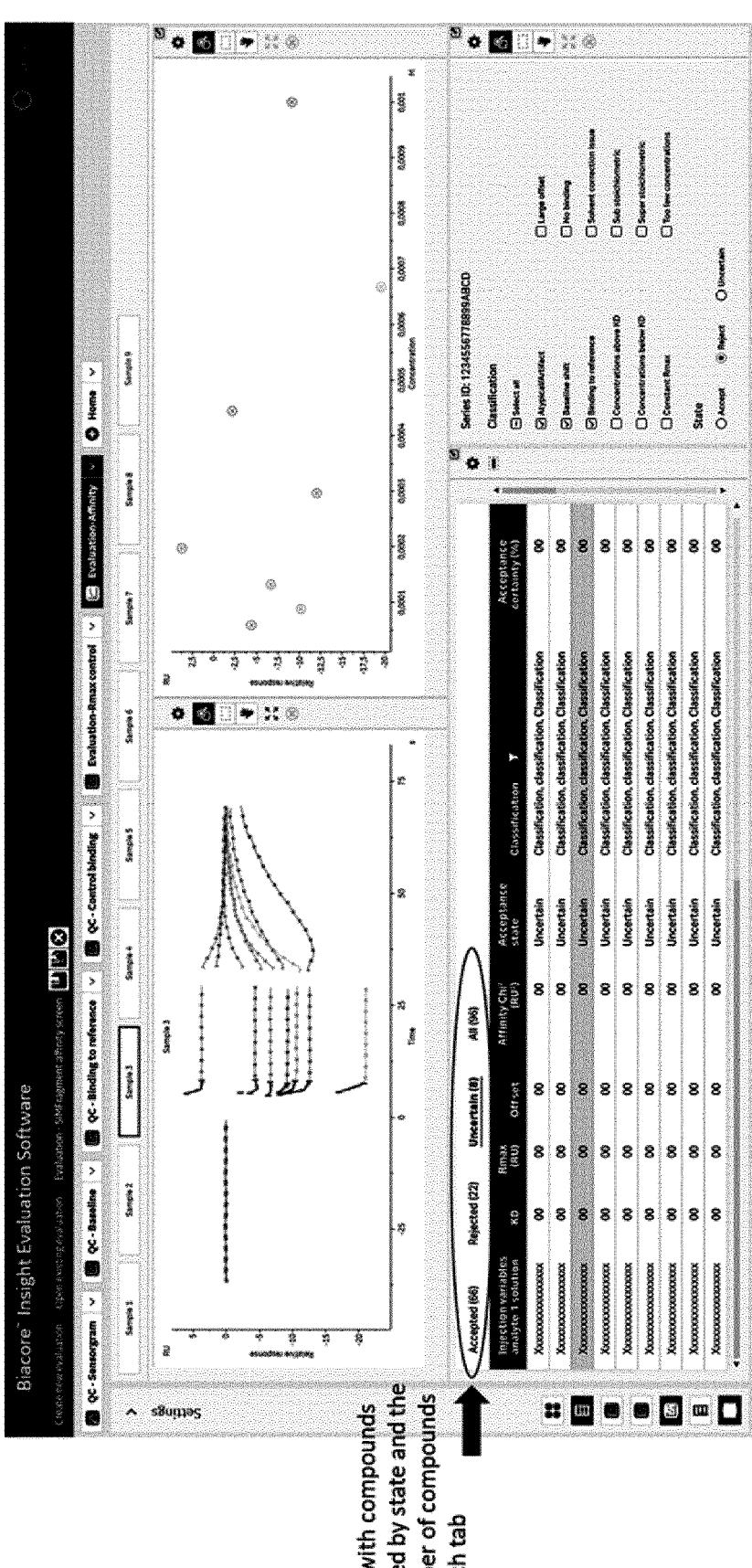
Figure 11E:
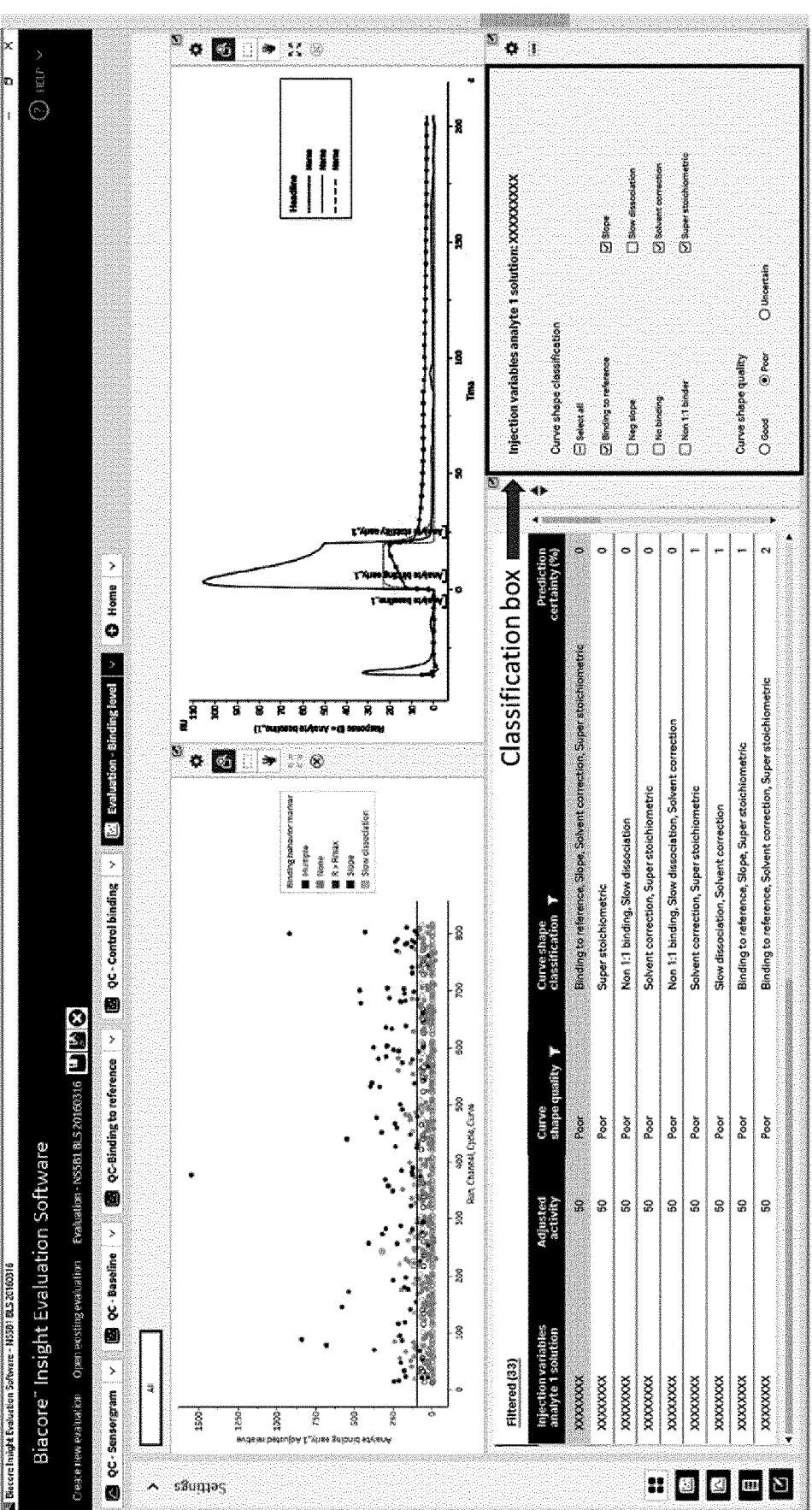

The method may also include tabs and filtering of data to view sets of classifications as in FIG. 11d.

A computer program may use graphical elements (FIGS. 11a-11c) to support parameter assignment, including comparison to theoretical binding curves, simultaneous display of binding and binding to reference, and/or lines in a dose response plot corresponding to KD values based on the use of different steady state models.

The machine learning algorithm may be selected from a group comprising decision trees, k nearest neighbour (kNN), random forest, K-means, gradient boosting algorithms, artificial neuronal network (ANN), deep learning algorithm, or any combination thereof.

The machine learning algorithm can be trained using data from one analyte sensor system and be used for classification of data from another analyte sensor system. Alternatively, data used for training and data to be classified by the machine learning algorithm may be obtained by the same system or at least same type of system.

When training the machine learning algorithm a second set of analyte sample solutions is used. The second set of analyte sample solutions may be different from the first set of analyte sample solutions in both number of analyte sample solutions and type of analytes. The ligand(s) used when training the machine learning algorithm may be the same as used for interaction with the first set of analyte sample solutions. The ligand(s) used may alternatively be ligand(s) not used for interaction with the first set of analyte sample solutions.

The second set of analyte sample solutions may comprise a plurality of different analyte sample solutions. Preferably, the second set of sample solutions comprises at least 10, at least 100 or at least 500 different analyte sample solutions. The larger number of analyte sample solutions used for the training the better the classification of analyte sample solutions of the first set of analyte sample solutions.

Which interaction parameters and how many interaction parameters per analyte sample solution to use for training the machine learning algorithm may be dependent on the aim of the use of the machine learning algorithm. Generally, a larger number of interaction parameters used for the training, the better the classification of analyte sample solutions of the first set of analyte sample solutions. Determining which interaction parameters and extracting these parameters may be performed by an expert user of the analytical system or by (an) ANN(s) or expert system(s) trained on a plurality of training sets of response data.

The type of interaction parameters used for training the machine learning algorithm may be the same as provided to the trained machine learning algorithm for the analyte sample solutions of the first set of analyte sample solutions. Alternatively, the number and/or type of interaction parameters used may differ. The machine learning algorithm may be trained on a larger set of interaction parameters than is used for the actual classification of the analyte sample solutions of the first set of analyte sample solutions.

The type of parameters discussed above extracted for the first set of analytical samples may, hence, be extracted from the second set of analytical samples for training of the machine learning algorithm. The machine learning algorithm may also be provided with, as discussed above, reference subtracted interaction parameters, reference interaction parameters, negative and positive interaction parameters, and solvent correction. The machine learning algorithm is also provided with for each analyte sample solution of the second set of analyte sample solutions at least one respective quality classification group indicative of the interaction of the analyte sample solution with the ligand. Determining the quality classification group of each analyte sample solution of the second set of analyte samples may be performed by an expert user of the analytical system or by (an) ANN(s) or expert system(s) trained on a plurality of training sets of response data.

The number of different quality classification groups may in one example be two, the first group comprising analytes of good enough interaction with the ligand (see FIG. 4*a* and FIG. 4*b*) of interest and the second group analytes of poor interaction with the ligand of interest (see FIGS. 5 and 6). A classification being good enough indicating that such analytes could be of interest for further analysis.

In another example, the number of quality classification groups may be 100, wherein group 1 comprises analytes of poor interaction with the ligand and group 100 analytes of very good interaction with the ligand.

That an analyte sample solution or series of solutions are classified into at least one quality classification group indicative of the interaction of the analyte sample solution with the ligand, could here involve a first classification into a main group, such as relevant or not for further analysis, and a second group informing about why the analyte sample solution was classified into the main group, e.g. due to non-specific binding, too low or high refractive index, binding to the ligand is not 1:1, no binding or very low binding response (below a predetermined cut line), high slope in association, slow dissociation, poor mixing, R>Rmax and the analyte being a super stoichiometric binder, concentrations above KD, too few concentrations to determine KD, unreliable parameters in steady state analysis.

The same machine learning could classify into several groups including hit/non hit and why it is a non-hit. An alternative is to train two machine learning algorithms, one for classification of analytes and one for explanation of why an analyte has received a classification as not being of relevance for further analysis and combine these trained machine learning algorithms. A statistic measure of each interaction parameter can be used when training the machine algorithm.

Such a trained machine learning algorithm will then return a classification of an analyte sample solution from the first set of analyte sample solutions into a quality classification group indicative of the interaction of the analyte sample solution with the ligand. In a BLS or affinity screen analysis, when hundreds of analyte sample solutions are to be analysed to provide an overview of a library of analyte candidates, the present method would provide a fast classification of analyte candidates as relevant or not for further processing. Further, the evaluation of candidate analytes is made less user dependent and not as experienced users may be assisted in the evaluation of monitored molecular interactions.

In a non-limiting example, a machine learning algorithm comprising a one hidden layer neural network with ten hidden neurons and a learning rate of 0.001 was used (here SciSharp.Tensorflow.Redist v1.15.1 and Tensorflow.NET v 0.13.0 nuget packages were used). For this example the interaction between different analyte sample solutions and a ligand being a hepatitis enzyme, NS5B1b (an RNA-dependent RNA polymerase, subtype 1b) were monitored. A data set comprising data for 457 analyte sample solutions, 64 positive controls and 136 negative controls, was divided into a training set (second set of analyte sample solutions) and a verification set (first set of analyte sample solutions), where 80% of the data was used for training and 20% of the data was used for verification.

Interaction parameters extracted and used for both the training and the verification were in this example: early binding response divided with late binding response of positive control, difference of binding late response and binding early response divided with the binding early response, stability early response, stability late response, difference of binding late response and stability early response, late binding response of reference, stability late response of reference, difference of late binding response of reference and early binding response of reference, binding early divided with an average binding of all negative controls with five standard deviations of all negative controls, and measured variation (standard deviation) of the early binding response.

Further, for each analyte sample solution used for the training a quality classification group indicative of the interaction of the analyte sample solution with the ligand was given to the machine learning algorithm. Here the sample solutions were classified in two quality classification groups, the first comprising analytes of good enough interaction with the ligand and the second group analytes of poor interaction with the ligand.

When running the verification data set on the thus trained machine learning algorithm, the specificity was 96% and the sensitivity 93%.

By continuous training and development of these models an experienced user can easily modify the outcome of the classification and retrain the model to better fit user preferences. Further, by using a trained machine learning algorithm as described above to classify detection analyte samples, the classification process may be speeded up, especially if there is a large amount analyte samples in an analysis, the evaluation results may be less user dependent and not as experienced users may be assisted in the evaluation of monitored molecular interactions.

Although the description above contains a plurality of specificities, these should not be construed as limiting the scope of the concept described herein but as merely providing illustrations of some exemplifying embodiments of the described concept. It will be appreciated that the scope of the presently described concept fully encompasses other embodiments which may become obvious to those skilled in the art, and that the scope of the presently described concept accordingly is not to be limited. Reference to an element in the singular is not intended to mean "one and only one" unless explicitly so stated, but rather "one or more". All structural and functional equivalents to the elements of the above-described embodiments that are known to those of ordinary skill in the art are expressly incorporated herein and are intended to be encompassed hereby.

The invention claimed is:

1. A method for classifying monitoring results from an analytical sensor system arranged to monitor a molecular interaction between an analyte and a ligand, wherein a set of response data representing progress of the molecular interaction with time is acquired, in turn, allowing a first set of analyte sample solutions to interact with a ligand and acquiring a corresponding set of response data for each monitored molecular interaction, extracting at least one interaction parameter from at least a portion of each set of acquired response data, for each analyte sample solution, providing a trained machine learning algorithm with the at least one extracted interaction parameter, and allowing the trained machine learning algorithm to classify each analyte sample solution, based on the at least one extracted interaction parameter, into at least one quality classification group indicative of the interaction of the analyte sample solution with the ligand, and extracting at least one negative control interaction parameter obtained from interaction of a negative control solution with the ligand and providing the at least one negative control interaction parameter to the trained machine learning algorithm, wherein the machine learning algorithm is trained using:

a set of interaction parameters extracted from at least a portion of acquired sets of response data obtained from interactions between a second set of analyte sample solutions with at least one ligand, for each analyte sample solution of the second set of analyte sample solutions, at least one respective quality classification group indicative of the interaction of the analyte sample solution with the ligand, and the at least one negative control interaction parameter.

2. The method of claim 1, wherein the at least one interaction parameter extracted from the set of acquired response data for an analyte sample solution of the first set of analyte sample solutions comprises 80-100% of the acquired response data.

3. The method of claim 1, wherein the at least one interaction parameter extracted from the set of acquired response data for an analyte sample solution of the second set of analyte sample solutions and used for training of the machine learning algorithm comprises 80-100% of the acquired response data.

4. The method of claim 1, wherein the at least one interaction parameter extracted from the set of acquired response data for an analyte sample solution of the first set of analyte sample solutions comprises any one or more the following interaction parameters extracted at defined time points in the response data, a) early binding response,
b) late binding response,
c) stability early response,
d) stability late response,
e) early binding response divided by molecular weight of the analyte,
f) late binding response divided by molecular weight of the analyte,
g) difference of binding late response and binding early response divided with the binding early response,
h) measured variation in any of interaction parameters a)-g), i) measured slope of any of the interaction parameters a)-g), and/or the interaction parameter comprises, when said analyte sample solution is constituted by a plurality of analyte sample solutions of different analyte concentrations of the same analyte:
j) equilibrium dissociation constant calculated using a maximum binding capacity from said plurality of analyte sample solutions.

5. The method of claim 1, wherein the at least one interaction parameter extracted from the second set of acquired response data for an analyte sample solution of the second set of analyte sample solutions and used for training of the machine learning algorithm comprises any one or more the following interaction parameters extracted at defined time points in the response data, a) early binding response,
b) late binding response,
c) stability early response,
d) stability late response,
e) early binding response divided by molecular weight of the analyte,
f) late binding response divided by molecular weight of the analyte,
g) difference of binding late response and binding early response divided with the binding early response,
h) measured variation in any of interaction parameters a)-g),
i) measured slope of any of the interaction parameters a)-g), and/or the interaction parameter comprises, when said analyte sample solution is constituted by a plurality of analyte sample solutions of different analyte concentrations of the same analyte:
j) equilibrium dissociation constant calculated using a maximum binding capacity from said plurality of analyte sample solutions.

6. The method of claim 1, further comprising for each of the analyte sample solutions of the first set of analyte sample solutions extracting at least one reference subtracted interaction parameter and providing this to the trained machine learning algorithm.

7. The method of claim 1, wherein the machine learning algorithm further is trained using, for each of the analyte sample solutions of the second set of analyte sample solutions, at least one reference subtracted interaction parameter.

8. The method of claim 1, further comprising for each of the analyte sample solutions of the first set of analyte sample solutions extracting at least one reference interaction parameter and providing the reference interaction parameter(s) to the trained machine learning algorithm, wherein the at least one reference interaction parameter comprises any one or more of:

k) early binding response of reference,
l) late binding response of reference,
m) stability early response of reference,
n) stability late response of reference, and
o) difference of binding late response of reference, and binding early response of reference, divided with the binding early response of reference, and/or the interaction parameter comprises, when said analyte sample solution is constituted by a plurality of analyte sample solutions of different analyte concentrations of the same analyte:
p) equilibrium dissociation constant calculated using a maximum binding capacity from said plurality of analyte sample solutions.

9. The method of claim 1, wherein the machine learning algorithm further is trained using, for each of the analyte sample solutions of the second set of analyte sample solutions, at least one reference interaction parameter, wherein the at least one reference interaction parameter comprises any one or more of:

k) early binding response of reference, l) late binding response of reference, m) stability early response of reference, n) stability late response of reference, and o) difference of binding late response of reference, and binding early response of reference, divided with the binding early response of reference, and/or the interaction parameter comprises, when said analyte sample solution is constituted by a plurality of analyte sample solutions of different analyte concentrations of the same analyte:

p) equilibrium dissociation constant calculated using a maximum binding capacity from said plurality of analyte sample solutions.

10. The method of claim 1, further comprising extracting at least one positive control interaction parameter obtained from interaction of a positive control sample solution with the ligand and providing the at least one positive control interaction parameter to the trained machine learning algorithm.

11. The method of claim 1, wherein the machine learning algorithm further is trained using at least one positive control interaction parameter obtained from interaction of a positive control sample solution with the ligand(s).

12. The method of claim 1, wherein the machine learning algorithm is selected from a group comprising decision trees, k nearest neighbour (kNN), random forest, K-means, gradient boosting algorithms, artificial neuronal network (ANN), deep learning algorithm, or any combination thereof.

13. An analytical sensor system for detecting molecular binding interactions between an analyte and a ligand and for classifying monitoring results, comprising:

a sensor device comprising a detector for monitoring a molecular interaction between a ligand and an analyte sample solution with time, a data producer unit arranged to produce response data representing the progress of the monitored molecular interaction with time, an extraction unit configured to extract at least one interaction parameter from at least a portion of the produced response data, wherein the at least one interaction parameter is a negative control parameter obtained from interaction of a negative control solution with the ligand, a data processing unit configured to receive said at least one interaction parameter and to provide a classification of the analyte sample solution into at least one quality classification group indicative of the interaction of the sample solution with the ligand and based on the at least one interaction parameter using a trained machine learning algorithm, wherein the trained machine learning algorithm is configured to be trained using the at least one interaction parameter.

14. The analytical sensor system of claim 13, further comprising a training centre for training of the machine learning algorithm by providing the machine learning algorithm with interaction parameters extracted from response data from a plurality of monitored analyte-ligand interactions together with at least one respective quality classification group indicative of the interaction of the analyte with the ligand.

15. A computer program comprising program code for performing the method of claim 1, when the program is run on a computer.

* * * * *